US011732006B2

(12) United States Patent
Gillberg et al.

(10) Patent No.: US 11,732,006 B2
(45) Date of Patent: *Aug. 22, 2023

(54) IBAT INHIBITORS FOR THE TREATMENT OF LIVER DISEASES

(71) Applicant: Albireo AB, Gothenburg (SE)

(72) Inventors: Per-Göran Gillberg, Mölndal (SE); Hans Graffner, Helsingborg (SE); Ingemar Starke, Gothenburg (SE)

(73) Assignee: Albireo AB, Gothenburg (SE)

( * ) Notice: Subject to any disclaimer, the term of this patent is extended or adjusted under 35 U.S.C. 154(b) by 105 days.

This patent is subject to a terminal disclaimer.

(21) Appl. No.: 17/206,925

(22) Filed: Mar. 19, 2021

(65) Prior Publication Data

US 2021/0340175 A1 Nov. 4, 2021

Related U.S. Application Data

(63) Continuation of application No. 16/737,742, filed on Jan. 8, 2020, now Pat. No. 10,981,952, which is a continuation of application No. 15/069,199, filed on Mar. 14, 2016, now Pat. No. 11,261,212, which is a continuation of application No. 13/881,447, filed as application No. PCT/SE2011/051335 on Nov. 8, 2011, now abandoned.

(60) Provisional application No. 61/410,957, filed on Nov. 8, 2010.

(30) Foreign Application Priority Data

Nov. 8, 2010 (SE) .................................. 1051165-7

(51) Int. Cl.
*A61P 35/00* (2006.01)
*A61K 31/55* (2006.01)
*A61K 31/554* (2006.01)
*A61K 31/575* (2006.01)
*A61K 38/05* (2006.01)
*C07K 5/065* (2006.01)
*C07K 5/062* (2006.01)
*A61K 38/00* (2006.01)

(52) U.S. Cl.
CPC .......... *C07K 5/06078* (2013.01); *A61K 31/55* (2013.01); *A61K 31/554* (2013.01); *A61K 31/575* (2013.01); *A61K 38/05* (2013.01); *A61P 35/00* (2018.01); *C07K 5/0606* (2013.01); *C07K 5/06026* (2013.01); *A61K 38/00* (2013.01); *A61K 2121/00* (2013.01)

(58) Field of Classification Search
CPC .. C07K 5/06026; C07K 5/0606; A61K 31/55; A61K 31/554; A61K 31/575; A61K 38/05; A61P 35/00
See application file for complete search history.

(56) References Cited

U.S. PATENT DOCUMENTS

| | | |
|---|---|---|
| 3,539,380 A | 11/1970 | Johnson |
| 4,172,120 A | 10/1979 | Todd et al. |
| 4,507,235 A | 3/1985 | Wunsch |
| 5,049,394 A | 9/1991 | Howard et al. |
| 5,167,965 A | 12/1992 | Schulz |
| 5,294,448 A | 3/1994 | Ring |
| 5,384,130 A | 1/1995 | Kamada |
| 5,422,124 A | 6/1995 | Valducci |
| 5,578,316 A | 11/1996 | Bhardwaj et al. |
| 5,681,584 A | 10/1997 | Savastano |
| 5,811,388 A | 9/1998 | Friend et al. |
| 5,900,233 A | 5/1999 | Day |
| 5,976,811 A | 11/1999 | Mullner et al. |
| 5,994,391 A | 11/1999 | Lee et al. |
| 6,069,167 A | 5/2000 | Sokol |
| 6,277,831 B1 | 8/2001 | Frick et al. |
| 6,346,527 B1 | 2/2002 | Takanaka et al. |
| 6,355,672 B1 | 3/2002 | Yasuma et al. |
| 6,387,924 B2 | 5/2002 | Lee et al. |
| 6,387,944 B1 | 5/2002 | Frick et al. |
| 6,426,340 B1 | 7/2002 | Gibson et al. |
| 6,592,900 B1 | 7/2003 | Buhler |
| 6,635,280 B2 | 10/2003 | Shell et al. |
| 6,676,979 B2 | 1/2004 | Marlett et al. |
| 6,906,058 B2 | 6/2005 | Starke et al. |
| 6,943,189 B2 | 9/2005 | Keller et al. |
| 7,019,023 B2 | 3/2006 | Frick et al. |
| 7,125,864 B2 | 10/2006 | Starke et al. |
| 7,132,416 B2 | 11/2006 | Starke et al. |
| 7,132,557 B2 | 11/2006 | Wilkes et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,514,421 B2 * | 4/2009 | Abrahamsson ........... A61P 1/04 514/211.1 |
| 7,767,229 B1 | 8/2010 | Milne et al. |
| 7,923,468 B2 | 4/2011 | Frick et al. |
| 7,939,061 B2 | 5/2011 | Prakash et al. |

(Continued)

FOREIGN PATENT DOCUMENTS

| | | |
|---|---|---|
| CA | 2065151 | 3/1991 |
| DE | 3930168 | 3/1991 |

(Continued)

OTHER PUBLICATIONS

[No Author Listed], "Practical Pharmaceutical Preparation Technology", People's Medical Publishing House, Jan. 1999, 286-287 (Machine Translation).

(Continued)

*Primary Examiner* — Jared Barsky
(74) *Attorney, Agent, or Firm* — Fish & Richardson P.C.

(57) ABSTRACT

The present invention regards specific IBAT inhibitors useful in the prophylaxis and/or treatment of a liver disease. It also relates to compositions comprising these IBAT inhibitors, a method for treatment of the disorders and a kit comprising the substances or the compositions.

10 Claims, No Drawings

(56) References Cited

U.S. PATENT DOCUMENTS

| | | |
|---|---|---|
| 8,048,413 B2 | 11/2011 | Huguet |
| 8,067,584 B2 | 11/2011 | Starke et al. |
| 9,023,368 B2 | 5/2015 | Basit et al. |
| 9,295,677 B2 | 3/2016 | Ling et al. |
| 9,409,875 B2 | 8/2016 | Bohlin et al. |
| 9,684,018 B2 | 6/2017 | Horanzy |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 10,093,697 B2 | 10/2018 | Gillberg et al. |
| 10,183,920 B2 | 1/2019 | Ymen et al. |
| 10,786,529 B2 | 9/2020 | Gillberg et al. |
| 10,793,534 B2 | 10/2020 | Gillberg |
| 10,941,127 B2 | 3/2021 | Gilberg et al. |
| 10,975,045 B2 | 4/2021 | Gillberg et al. |
| 10,975,046 B2 | 4/2021 | Lundqvist et al. |
| 10,981,952 B2 | 4/2021 | Gilberg et al. |
| 10,995,115 B2 | 5/2021 | Bhat et al. |
| 11,007,142 B2 | 5/2021 | Gillberg et al. |
| 11,014,898 B1 | 5/2021 | Gillberg et al. |
| 11,111,224 B2 | 9/2021 | Gillberg |
| 11,180,465 B2 | 11/2021 | Gillberg et al. |
| 11,225,466 B2 | 1/2022 | Gillberg et al. |
| 2002/0054903 A1 | 5/2002 | Tyler et al. |
| 2002/0142054 A1 | 10/2002 | Marlett et al. |
| 2003/0124088 A1 | 7/2003 | Masuda et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0153607 A1 | 8/2003 | Glinecke |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1* | 4/2004 | Starke ............... A61P 9/02 514/211.09 |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0089572 A1 | 4/2005 | Kumar |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2005/0282822 A1 | 12/2005 | Alstermark et al. |
| 2005/0287178 A1* | 12/2005 | Steed ............... A61B 8/08 424/400 |
| 2006/0083790 A1 | 4/2006 | Anderberg et al. |
| 2006/0210631 A1 | 9/2006 | Patel |
| 2006/0210633 A1 | 9/2006 | Dharmadhikari |
| 2007/0197522 A1 | 8/2007 | Edwards et al. |
| 2007/0237818 A1 | 10/2007 | Malcom et al. |
| 2008/0193543 A1 | 8/2008 | Morello |
| 2008/0207592 A1 | 8/2008 | Frick et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2011/0003782 A1 | 1/2011 | Pellicciari |
| 2011/0152204 A1 | 6/2011 | Gedulin et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0052269 A1 | 2/2013 | Lescure |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2014/0275090 A1 | 9/2014 | Gedulin et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0264029 A1 | 9/2018 | Gillberg et al. |
| 2018/0264030 A1 | 9/2018 | Gillberg et al. |
| 2018/0264031 A1 | 9/2018 | Gillberg et al. |
| 2018/0360869 A1 | 12/2018 | Gillberg et al. |
| 2018/0360870 A1 | 12/2018 | Gillberg et al. |
| 2018/0360871 A1 | 12/2018 | Gillberg et al. |
| 2018/0362577 A1 | 12/2018 | Gillberg et al. |
| 2019/0046451 A1 | 2/2019 | Gillberg et al. |
| 2020/0002299 A1 | 1/2020 | Lundqvist |
| 2020/0046635 A1 | 2/2020 | Gillberg et al. |
| 2020/0046636 A1 | 2/2020 | Gillberg et al. |
| 2020/0046757 A1 | 2/2020 | Gillberg et al. |
| 2020/0046758 A1 | 2/2020 | Gillberg et al. |
| 2020/0049611 A1 | 2/2020 | Gillberg et al. |
| 2020/0140484 A1 | 5/2020 | Gillberg et al. |
| 2020/0247768 A1 | 8/2020 | Gillberg et al. |
| 2020/0247769 A1 | 8/2020 | Gillberg et al. |
| 2020/0330545 A1 | 10/2020 | Gillberg et al. |
| 2021/0147372 A1 | 5/2021 | Gillberg |
| 2021/0171479 A1 | 6/2021 | Gillberg |
| 2021/0171480 A1 | 6/2021 | Gillberg |
| 2021/0171481 A1 | 6/2021 | Gillberg |
| 2021/0171482 A1 | 6/2021 | Gillberg |
| 2021/0171483 A1 | 6/2021 | Gillberg |
| 2021/0177767 A1 | 6/2021 | Byrod |
| 2021/0179572 A1 | 6/2021 | Gillberg |
| 2021/0236511 A1 | 8/2021 | Byrod |
| 2021/0299141 A1 | 9/2021 | Gillberg |
| 2021/0387956 A1 | 12/2021 | Gillberg |
| 2022/0041567 A1 | 2/2022 | Gillberg et al. |
| 2022/0143043 A1 | 5/2022 | Gillberg |

FOREIGN PATENT DOCUMENTS

| | | |
|---|---|---|
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1045840 | 10/2000 |
| EP | 1273307 | 1/2003 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | A-2004-516285 | 6/2004 |
| JP | B-3665055 | 6/2005 |

(56) References Cited

FOREIGN PATENT DOCUMENTS

| | | |
|---|---|---|
| JP | 2006/124695 | 5/2006 |
| JP | B-4870552 | 2/2012 |
| JP | 2013-541584 | 11/2013 |
| JP | A-2013-542953 | 11/2013 |
| JP | B-5421326 | 2/2014 |
| JP | H02258719 | 10/2019 |
| RU | 2314104 | 1/2008 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/09815 | 4/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |
| WO | WO 2004/020421 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2011/137135 | 11/2011 |
| WO | WO 2011/150286 | 12/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2014/174066 | 10/2014 |
| WO | WO 2014/179453 | 11/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |
| WO | WO 2020/167964 | 8/2020 |
| WO | WO 2020/167981 | 8/2020 |
| WO | WO 2020/167985 | 8/2020 |

OTHER PUBLICATIONS

A Long-Term, Open-Label Study of LUM001 With a Double-Blind, Placebo Controlled, Randomized Drug Withdrawal Period to Evaluate Safety and Efficacy in Children With Alagille Syndrome (ICONIC), Clinical Trials.gov, Jun. 9, 2014, retrieved Oct. 3, 2014, http://clinicaltrials.gov/ct2/show/NCT02160782?term=LUM001&rank=7, 4 pages.

AASLD: 2017 68th Annual Meeting of the American Association for the Study of Liver Diseases, Washington, DC, Oct. 20-24, 2017, (Abstract only).

Adams et al., "Hepascore: an accurate validated predictor of liver fibrosis in chronic hepatitis C infection," Clin. Chem. 2005, vol. 51(10), p. 1867-1873.

Alagile Syndrome, Wikipedia, the free encyclopedia, posted on or about Feb. 11, 2005, retrieved Feb. 12, 2014, http://en.wikipedia.org/wiki/Alagille_syndrome, 3 pages.

Alashkar et al., "Meeting Info.: 57th Annual Meeting of the AmericanSociety-of-Hematology," Orlando, FL, USA. Dec. 5-8, 2015, Amer Soc Hematol, Blood, 2015, 126(23).

Albireo's Lead Compound in Cholestatic Liver Diseases, A4250, Projects Against Bile Acid-Mediated Cholestatic Liver Injury in Mice, Albireo Press Release, Apr. 11, 2014, 2 pages.

Alissa et al., "Invited Review: Update on Progressive Familial Intrahepatic Cholestasis," Journal of Pediatric Gastroenterology and Nutrition, 2008, 46:241-252.

Allison et al., "Studies on mixed populations of human intestinal bacteria grown in single-stage and multistage continuous culture systems," Appl. Environ. Microbial. 1989, 55(3):672-678.

Alnouti, "Bile acid sulfation: a pathway of bile acid elimination and detoxification," Toxicological Sciences, 2009, 108(2):225-246.

Alonso et al., "Histologic pathology of the liver in progressive familial intrahepatic cholestasis," Journal of Pediatric Gastroenterology and Nutrition, 14: 128-133, 1994.

Alvarez et al., "Reduced hepatic expression of farnesoid X receptor in hereditary cholestasis associated to mutation in ATP8B1," Hum Mol Genet, 2004, 13(20):2451-2460.

Alvarez, "Development of crystallization processes for pharmaceutical applications," LACCEI, 2007, 2E.3-1-2E.3-9.

Alvarez, Fernando; "Treatments in chronic cholestasis in children." Ann. Nestlé (2008) 66 p. 127-135.

American Diabetes Association, "Management of Dyslipidemia in Adults with Diabetes," Diabetes Care, Jan. 2003, 26(1).

An Extension Study to Evaluate the Long-Term Safety and Durability of Effect of LUM001 in the Treatment of Cholestatic Liver Disease in Subjects With Alagille Syndrome (IMAGINE), Clinical Trials.gov, Jan. 23, 2014, retrieved on Oct. 3, 2014, http://clinicaltrials.gov/ct2/show/NCT02047318?term=LUM001&rank=3, 3 pages.

An Extension Study to Evaluate the Long-Term Safety and Durability of Effect of LUM001 in the Treatment of Cholestatic Liver Disease in Subjects With Alagille Syndrome (IMAGINE-II), Clincal Trials.gov, Apr. 16, 2014, retrieved on Oct. 3, 2014, http://clinicaltrials.gov/ct2/show/NCT02117713?term=LUM001&rank=2, 3 pages.

Anakk et al., "Bile acids activate YAP to promote liver carcinogenesis," Cell Rep., Nov. 27, 2013, 5(4):1060-1069.

Angulo et al., "Independent Predictors of Liver Fibrosis in Patients With Nonalcoholic Steatohepatitis," Hepatology, Dec. 1999, 30(6): 1356-1362.

Angulo et al., "The NAFLD fibrosis score: a noninvasive system that identifies liver fibrosis in patients with NAFLD," Hepatology, 2007, vol. 45(4), p. 846-54.

(56) References Cited

OTHER PUBLICATIONS

Angulo, "Use of ursodeoxycholic acid inpatients with liver disease," Current Gastroenterology Reports, Feb. 1, 2002, 4(1):37-44.
Anzivino et al., "ABCB4 and ABCB11 mutations in intrahepatic cholestasis of pregnancy in an Italian population," Dig Liver Dis., 2013, 45(3):226-232.
Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.
Arnell et al., "Follow-up in children with progressive familial intrahepatic cholestasis after partial external biliary diversion," J Pediatr Gastroenterol Nutr., 2010, 51(4):494-499.
Artursson and Karlsson, "Correlation Between Oral Drug Absorption in Humans and Apparent Drag Permeability Coefficients in Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibito A4250 protects against bile acid-mediated cholestatic liver injury in mice," J. Hepatology, 2014, 60:S57.
Baghdasaryan et al., "Inhibition of intestinal bile acid absorption by ASBT inhibitor A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Balbach et al., "Pharmaceutical evaluation of early development candidates "the 100 mg-approach"," Int J Pharm, May 4, 2004, 275(1):1-12.
Banker et al., "Modem Pharmaceutics, 3ed", Marcel Dekker, New York, 1996, pp. 451 and 596.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Bavin, "Polymorphism in Process Development," Chemistry and Industry, 527-529, 1989.
Beausejour et al., "Description of two new ABCB11 mutations responsible for type 2 benign recurrent intrahepatic cholestasis in a French-Canadian family," Can J Gastroenterol., 2011, 25(6):311-314.
Beraza et al., Nor-ursodeoxycholic acid reverses hepatocyte-specific nemo-dependnt steatohepatitis. Gut, 2011: 60: 387-396.
Bhaskaran et al., "Extrusion Spheronization—A Review," International Journal of PharnnTech Research.vol. 2, No. 4, pp. 2429-2433, Oct.-Dec. 2010 (Year: 2010).
Billington et al., "Effects of bile salts on the plasma membranes of isolated rat hepatocytes," Bichem. J. 188: 321-327, 1980.
Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Board of Appeal of European Patent Office, Case No. T 077/08-3.3.01, dated May 24, 2011, 17 pages.
Boncristani et al., Respiratory Viruses, Encyclopedia of Microbiology, 2009, 19 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Bounford. University of Birmingham. Dissertation Abstracts International, (2016) vol. 75, No. 1C. Order No. AA110588329. ProQuest Dissertations & Theses.
Bowel Diversion Surgeries: Ileostomy, Colostomy, Ileoanal Reservoir and Continent Ileostomy, US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
Brunt et al., "Nonalcoholic Steatohepatitis: A Proposal for Grading and Staging the Histological Lesions," American Journal of Gastroenterology, Sep. 1999, 94(9): 2467-2474.
Brunzell and Hokanson, "Dislipidemia of Central Obesity and Insulin Resistance," Diabetes Care, 1999, 22(Suppl. 3):C10-C13.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Burrows, "Interventions for treating cholestasis in pregnancy," Cochrane Database Syst. Rev., 4:CD00493, 2001.
Byrn et al., "Pharmaceutical Solids: A Strategic Approach to Regulatory Considerations," Pharmaceutical Research, 1995, 12(7), pp. 945-954.
Byrne et al., "Missense mutations and single nucleotide polymorphisms in ABCB11 impair bile salt export pump processing and function or disrupt pre-messenger RNA splicing," Hepatology., 2009, 49(2):553-567.
Caira, "Crystalline Polymorphism of Organic Compounds," in: Topics in Current Chemistry, Jan. 1998, 198:163-208.
Camilleri, "Probiotics and irritable bowel syndrome: rationale, putative mechanisms, and evidence of clinical efficacy," Clin. Gastroenterol., 40(3):264-9, Mar. 2006.
Carulli et al., "Review article: effect of bile salt pool composition on hepatic and biliary functions," Aliment. Pharmacol. Ther. 2000, vol. 14, suppl. 2, p. 14-18.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.
Chang et al., "Bile acids promote the expression of hepatitis c virus in replicon-harboring cells," Journal of Virology, Sep. 2007, 81(18):9633-9640.
Chauhan et al., "Pharmaceutical polymers," Encycl. Biomed. Polymers and Polymeric Biomaterials, 2016, 5929-5942.
Chen et al., "Bile salt export pump is dysregulated with altered farnesoid X receptor isoform expression in patients with hepatocelular carcinoma," Hepatologu, 57: 4, 1530-1541, 2013.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chen et al., "Serum and urine metabolite profiling reveals potential biomarkers of human hepatocellular carcinoma," Molecular and Cellular Proteomics 10.7, 2011.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.
Chiang, "Bile acids: regulation of synthesis," J. Lipid Res, 2009, 50(10):1955-1966.
Chourasia et al., "Polysaccharides for colon targeted drug delivery," Drug Delivery, Academic Press, vol. 11, No. 2, Jan. 1, 2004, 129-148, XP008060983.
Colorcon.com[online] "Achieving tablet stability with moisture management," retrieved on May 28, 2021, retrieved from URL<https://www.colorcon.com/connect-with-colorcon/achieving-tablet-stability-with-moisture-management>, 4 pages.

(56) References Cited

OTHER PUBLICATIONS

Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platform," PLoS One, 2017, 12(6):e0179200.
Das & Kar., "Non alcoholic steatohepatitis," JAPI. 53:, Mar. 2005.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," Hepatology: Autoimmune, Cholestatic and Biliary Disease, May 2010, 1645-1655.
Davit-Spraul et al., "Liver transcript analysis reveals aberrant splicing due to silent and intronic variations in the ABCB11 gene," Mol Genet Metab., 2014, 113(3):225-229.
Davit-Spraul et al., "Progressive familial intrahepatic cholestasis," Orphanet Journal of Rare Diseases, Jan. 2009, 4:1-12.
Dawson et al., "Bile acid transporters" J. Lipid Res. 2009, 50, 2340-2357.
Dawson, "Role of the intestinal bile acid transporters in bile acid and drug disposition," Handb. Exp. Pharmacol. 2011, 201:169-203.
De Lédinghen et al., "Controlled attenuation parameter for the diagnosis of steatosis in non-alcoholic fatty liver disease," J Gastroenterol Hepatol., 2016, 31(4):848-855.
DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-invasive Quantitative Assessment of Liver Fat by Ultrasound Imaging," Ultrasound Med Biol., 2018, 44(8):1585-1596.
Di Padova et al., "Double-blind placebo-controlled clinical trial of microporous chlestyramine in the treatment of intra- and extrahepatic cholestasis: relationship between itching and serum bile acids," Methods Find Exp Clin Pharmacol., Dec. 1984, 6(12):773-776 (Abstract Only).
Dibaise et al., "Bile Acids: An Underrecognized and Underappreciated Cause of Chronic Diarrhea", Pract. Gastroenterol, vol. 36(10), p. 32-44, 2012.
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drugs as inhibitors of the human sodium taurocholate cotransporting polypeptide (NTCP).," Mol. Pharm. 2013, 10(3):1008-1019.
Dongiovanni et al., "Genetic Predisposition in NAFLD and NASH: Impact on Severity of Liver Disease and Response to Treatment," Curren Pharma Design, 2013, 19:5219-5238.
Droge et al., "Exon-skipping and mRNA decay in human liver tissue: molecular consequences of pathogenic bile salt export pump mutations," Sci Rep., 2016, vol. 6: 24827.
Droge et al., "Sequencing of FIC1, BSEP and MDR3 in a large cohort of patients with cholestasis revealed a high number of different genetic variants," J Hepatol. 2017, 67(6):1253-1264.
Droge et al., Zeitschrift fur Gastroenterologie 2015, 53(12) Abstract No. A3-27. Meeting Info: 32. Jahrestagung der Deutschen Arbeitsgemeinschaft zum Studium der Leber. Dusseldorf, Germany. Jan. 22, 2016-Jan. 23, 2016.
Drumond et al., "Patients' appropriateness, acceptability, usability and preferences for pharmaceutical preparations: Results from a literature review on clinical evidence," Int. J. Pharm. 2017, 521(1-2):294-305.

EASL Clinical Practice Guidelines: Management of cholestatic liver diseases, European Assoc. for the Study of the Liver, Journal of Hepatology, 2009, 51:237-267.
Einspahr et al., "Protective role of wheat bran fiber: data from marker trials," Am. J. Med., 106(1A):32s-37s, Jan. 1999.
Eisai CO., Ltd., "Results from two phase 3 clinical trials of chronic constipation treatment "GOOFICE 5 mg tablet, The Lancet Gastro & Hepat., Jul. 9, 2018, 3 pages.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Ellinger et al., "Partial external biliary diversion in bile salt export pump deficiency: Association between outcome and mutation," World J Gastroenterol., 2017, 23(29):5295-5303.
Ellis et al., "Zebrafish abcb11b mutant reveals strategies to restore bile excretion impaired by bile salt export pump deficiency," Hepatology, 2018, 67(4)1531-1545.
Engelen et al., "Oral size perception of particles: effect of size, type, viscosity and method," J. Text. Studies 2005, 36(4):373-386.
Espenshade and Hughes, "Regulation of Sterol Synthesis in Eukaryotes," Annu. Rev. Genet., 2007, 41:401-427.
Evaluation of LUM001 in the Reduction of Pruritus in Alagille Syndrome (ITCH), Clinical Trials.gov, Feb. 5, 2014, retrieved on Oct. 3, 2014, http://clinicaltrials.gov/ct2/show/NCT02057692?term=LUM001&rank=5, 4 pages.
Evason et al., "Morphologic findings in progressive familial intrahepatic cholestasis 2 (PFIC2): correlation with genetic and immunohistochemical studies," Am J Surg Pathol., 2011, 35(5):687-696.
Evonik Industries, "Eudragit FS 30 D," Jul. 9, 2008, http://www.pharma-polymers.com.pharmapolymers/MCMbase/Pages/ProvideResource.aspx?respath-/NR/rdonlyres/BDD7E168-922E-4AB1-861F-EEEB58B85642/0/EUDRAGITFS30D_Promotiondatasheet_09072008.
Extended European Search Report in European Application No. 11840392.2, dated Feb. 24, 2014, 7 pages.
Extended European Search Report in European Application No. 11840481.3, dated Feb. 13, 2014, 10 pages.
Faubion et al., "Toxic bile salts induce rodent hepatocyte apoptosis via direct activation of Fas," The Journal of Clinical Investigation, 103: 1, 137-145, 1999.
Ferreira et al., Pediatric Transplantation 2013, 17(Suppl. 1):99. Abstract No. 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Fisher, "Milling of inactive pharmaceutical ingredients," Encyclopedia of Pharm. Tech., 2001, 2339-2351.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Forner et al., "Treatment of hepatocellular carcinoma," Critical Reviews in Oncology/Hematology, 2006, 60:89-98.
Francalanci et al., "Progressive familial intrahepatic cholestasis: Detection of new mutations and unusal modality of transmission," Digestive and Liver Disease 2010, 42(Suppl. 1):516, Abstract No. T.N.5.
Francalanci et al., Laboratory Investigation 2011, vol. 91, Supp. Suppl. 1, pp. 360A. Abstract No. 1526.
Fuentes-Zaragoza al., "Resistant Starch as functional ingredient: A review", , Food Research International, 43, 931-942, 2010.
Fuller, "Probiotics in man and animals," Appl. Bacterial. 1989, 66(5):365-378.
Gao et al., "Detection of hepatitis in children with idiopathic cholestatic bile salt export pump gene mutations," Shandong Yiyao, 2012, 52(10):14-16.
Gao et al., "Recent developments in the crystallization process: toward the pharmaceutical industry," Engineering, 2017, 3:343-353.
Gao et al., "The Identification of Two New ABCB11 Gene Mutations and the Treatment Outcome in a Young Adult with Benign

(56) References Cited

OTHER PUBLICATIONS

Recurrent Intrahepatic Cholestasis: A Case Report," Hepatitis Monthly 2017, 17(10):e55087/1-e55087/6.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gibson and Roberfroid, "Dietary modulation of the human colonic microbiota: introducing the concept of prebiotics," J. Nutr. 1995, 125(6):1401-1412.
Gillberg et al., "The IBAT Inhibition by A3309—A Potential Mechanism for the Treatment of Constipation," Gastroenterology, 2010, 138(5), Supp 1, S-224.
Giovannoni et al., "Genetics and Molecular Modeling of New Mutations of Familial Intrahepatic Cholestasis in a Single Italian Center," PLoS One, 2015, 10(12):e0145021.
Glagov et al., "Compensatory enlargement of human athersclerotic coronary arteries," N Engl. J. Med., May 1987, 316(22):1371-1375 (Abstract Only).
Goldschmidt et al., "Increased frequency of double and triple heterozygous gene variants in children with intrahepatic cholestasis," Hepatol Res., 2016, 46(4):306-311.
Govers et al., "Characterization of the adsorption of conjugated and unconjugated bile acids to insoluble, amorphous calcium phosphate", Journal of Lipid Research 35(5):741-748, 1994.
Greten, "Molecular therapy for the treatment of hepatocellular carcinoma," Br. J. Cancer, 2009, 100:19-23.
Griffin, et al., "A novel gene mutation in ABCB11 in siblings with progessive familial intrahepatic cholestasis type 2," Canadian Journal of Gastroenterology and Hepatology 2016, vol. 2016. Abstract No. A200. Meeting Info: 2016 Canadian Digestive Diseases Week, CDDW 2016. Montreal, QC, United States. Feb. 26-2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchuang Erke Zazhi, 2013, 31(10):905-909.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.
Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.
Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.
Hasegawa et al., "Intractable itch relieved by 4-phenylbutyrate therapy in patients with progressive familial intrahepatic cholestasis type 1," Orphanet J Rare Dis., 2014, 9:89.
Hayashi et al., "Assessment of ATP8B1 Deficiency in Pediatric Patients With Cholestasis Using Peripheral Blood Monocyte-Derived Macrophages," EBioMedicine, 2018, 27:187-199.
Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.
Heathcote, "Management of primary biliary cirrhosis," Hepatology, 2000, 31(4):1005-1013.
hepc.liverfoundation.org' [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.
Herbst et al., "Taking the next step forward—Diagnosing inherited infantile cholestatic disorders with next generation sequencing," Mol Cell Probes, 2015, 29(5):291-298.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Ho et al., "Polymorphic variants in the human bile salt export pump (BSEP; ABCB11): functional characterization and interindividual variability," Pharmacogenet Genomics, 2010, 20(1):45-57.
Hoffman et al., Human Anatomy, picture of the colon, p. 1-7, https://www.webmd.com/digestive-disorders/picture-of-the-colon#1, Accesses Aug. 4, 2019.
Hollands et al., "Ileal exclusion for Byler's disease: an alternative surgical approach with promising early results for pruritis," Journal of Pediatric Surgery, Feb. 1988, 33(2): 220-224.
Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.
Holz et al., "Plasma separation and anion adsorption results in rapid improvement of nasobiliary drainage (NBD)-refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie—10. Herbsttagung derDeutschen Gesellschaft fur Allgemein- und Viszeralchirurgie. Hamburg, Germany. Sep. 21, 2016-Sep. 24, 2016.
Hsu et al., "Adult progressive intrahepatic cholestasis associated with genetic variations in ATP8B1 and ABCB11," Hepatol Res., 2009, 39(6):625-631.
Hu et al., "Diagnosis of ABCB11 gene mutations in children with intrahepatic cholestasis using high resolution melting analysis and direct sequencing," Mol Med Rep., 2014, 10(3):1264-1274.
Huang et al., "Discovery of Potent, Nonsystemic Apical Sodium-Codependent Bile Acid Transporter Inhibitors (Part 2)," J. Med. Chem., 2005, 48:5853-5868.
IBAT inhibitor A4250 for Cholestatic Pruritus, ClinicalTrials.gov, Last updated Feb. 10, 2015, https://clinicaltrials.gov/ct2/show/NCT02360852?term=a4250&rank-1, 3 pages.
Imagawa et al., "Clinical phenotype and molecular analysis of a homozygous ABCB11 mutation responsible for progressive infantile cholestasis," J Hum Genet. 2018, 63(5):569-577.
Imagawa et al., "Generation of a bile salt export pump deficiency model using patient-specific induced pluripotent stem cell-derived hepatocyte-like cells," Sci Rep., 2017, 7:41806.
Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016.
Initiation of a Phase II Trial for A4250, the Company's Lead Compound for Cholestatic Liver Diseases and NASH, Albireo Phanna Press Release, Feb. 5, 2015, http://www.alberiopharma.com/News.aspx?PageID=1600872, 2 pages.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 10 pages.
International Search Report and Written Opinion for Application No. PCT/EP2014/058432, dated Jul. 11, 2014, 9 pages.

(56) References Cited

OTHER PUBLICATIONS

International Search Report and Written Opinion for Application No. PCT/SE2017/050126, dated Apr. 24, 2017, 27 pages.
International Search Report and Written Opinion for Application No. PCT/SE2017/050127, dated May 8, 2017, 16 pages.
International Search Report and Written Opinion for Application No. PCT/SE2017/050128, dated May 8, 2017, 16 pages.
International Search Report and Written Opinion for Appln. No. PCT/EP2019/064602, dated Aug. 9, 2019, 10 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12 pages.
International Search Report and Written Opinion for International Application No. PCT/SE2011/051366, dated Feb. 22, 2012, 18 pages.
International Search Report and Written Opinion in Appln. No. PCT/EP2021/071618, dated Oct. 4, 2021, 13 pages.
International Search Report and Written Opinion in Appln. No. PCT/SE2019/050603, dated Sep. 18, 2019, 11 pages.
International Search Report and Written Opinion in International Application No. PCT/SE2018/050802, dated Oct. 26, 2018, 14 pages.
International Search Report and Written Opinion in International Application No. PCT/SE2018/050803, dated Oct. 26, 2018, 14 pages.
International Search Report and Written Opinion in International Appln. No. PCT/EP2020/052940, dated Mar. 23, 2020, 12 pages.
International Search Report and Written Opinion in International Appln. No. PCT/EP2020/052942, dated Mar. 23, 2020, 9 pages.
International Search Report, Application No. PCT/JP2015/068240, dated Sep. 15, 2015, 11 pages (with English translation).
Ishak et al., "Histological grading and staging of chronic hepatitis," J. Hepatol. 1995, vol. 22, p. 696-699.
Ishibashi et al., "Hypercholesterolemia in low density lipoprotein receptor knockout mice and its reversal by adenovirus-mediated gene delivery", Journal of Clinical Investigation 92(2):883-893, 1993.
Islam and Di Baise, "Bile Acids: An underrecognized and under-appreciated cause of chronic diarrhea," Pract. Gastroenterol. 2012, vol. 36(10), p. 32-44.
Ivashkin et al., "A novel mutation of ATP8B1 gene in young patient with familial intrahepatic cholestasis.," Hepatology International 2016, 10(1):S461, Abstract No. LBO-38. Meeting Info: 25th Annual Conference of the Asian Pacific Association for the Study of the Liver, APASL 2016. Tokyo, Japan. Feb. 20, 2016-Feb. 24, 2016.
Jacobsen et al., "Effect of enterocoated cholestyramine on bowel habit after ileal resection: a double blind crossover study," Br. Med. J. 1985, vol. 290, p. 1315-1318.
Jacquet et al., "Alagille Syndrome in Adult Patients: It is Never Too Late," American Journal of Kidney Diseases, May 2007, 49(5):705-709.
Jankowska et al., "[Cholestatic liver disease in children]," Przegl. Epidemiol., 56:16-21, 2002.
Jankowska et al., "Ileal exclusion in children with progressive familial intrahepatic cholestasis," J Pediatr Gastroenterol Nutr. 2014, 58(1):92-95.
Jansen et al., "Endogenous bile acids as carcinogens," Journal of Hepatology, Sep. 2007, 47(3):434-435.
Jaquotot-Haerranz et al., "Clinical variability of mutations in the ABCB11 gene: a case report," Rev Esp Enferm Dig., 2013, 105(1):52-54.
Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.
Jiang et al., "Non alcoholic steatohepatitis a precursor for hepatocellular carcinoma development," World Journal of Gastroenterology: WJG, Nov. 28, 2014, 20(44):16464-16473.
Jirsa et al., "Indel in the FIC1/ATP8B1 gene—a novel rare type of mutation associated with benign recurrent intrahepatic cholestasis," Hepatol Res. 2004, 30(1):1-3.
Jung et al., "Prenatal molecular diagnosis of inherited cholestatic diseases," J Pediatr Gastroenterol Nutr. 2007, 44(4):453-458.
Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.
Kang et al., "Progressive Familial Intrahepatic Cholestasis in Korea: A Clinicopathological Study of Five Patients," J Pathol Transl Med. May 16, 2019, 53(4):253-260.
Karpen and Dawson, "Not all (bile acids) who wander are lost: the first report of a patient with an isolated NTCP defect," Hepatology, 2015, 61(1):24-27.
Khosla et al., "Recurrent Post-partum Jaundice: Rare Genetic Disorder With Novel Genetic Mutations Identified," American Journal of Gastroenterology 2015, 110(1):S397. Meeting Info.: 80th Annual Scientific Meeting of the American-College-of-Gastroenterology. Honolulu, HI, USA. Oct. 16-21, 2015.
Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.
Kleiner et al., "Design and validation of a histological scoring system for nonalcoholic fatty liver disease," Hepatology, 2005, 41(6):1313-1321.
Klomp et al., "Characterization of mutations in ATP8B1 associated with hereditary cholestasis," Hepatology, 2004, 40(1):27-38.
Knisely et al., "Hepatocellular Carcinoma in ten children under five years of age with bile salt export pump deficiency," Hepatology, Aug. 2006, 44(2):478-486.
Kolter et al., "Structure and dry binding activity of different polymers, including Kollidon VA 64," Drug Development, 2000, 26(11):1159-65.
Kooistra, et al., "KLIFS: A structural kinase-ligand interaction database," Nucleic Acids Res., 2016, vol. 44, No. D1, pp. D365-D371.
Korman et al., "Assessment of Activity in Chronic Active Liver Disease," New England Journal of Medicine, 2010, 290(25):1399-1402.
Kosters et al., "Bile acid transporters in health and disease," Xenobiotica 2008, 38(7-8):1043-1071.
Kozarewicz, "Regulatory perspectives on acceptability testing of dosage forms in children," Int. J. Pharm. 2014, 469(2):245-248.
Krawczyk et al., "Prolonged cholestasis triggered by hepatitis A virus infection and variants of the hepatocanalicular phospholipid and bile salt transporters," Ann Hepatol., 2012, 11(5):710-744.
Kumar and Tandon, "Use of ursodeoxycholic acid in liver diseases," J. Gastroenterology and Hepatology, 2001, 16:3-14.
Kumar et al., "Cholestatic presentation of chronic hepatitis c." Dig. Dis.Sci, 2001, 46(10):2066-2073.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Kurbegov et al., Biliary diversion for progressive familial intrahepatic cholestasis: Improved liver morphology and bile acid profile, Gastroenterology, 125: 4, 1227-1234, 2003.
Lam et al., "A patient with novel ABCB11 gene mutations with phenotypic transition between BRIC2 and PFIC2," J Hepatol. 2006, 44(1):240-242.
Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.

(56) References Cited

OTHER PUBLICATIONS

Lang et al,. "Genetic variability, haplotype structures, and ethnic diversity of hepatic transporters MDR3 (ABCB4) and bile salt export pump (ABCB11)," Drug Metab Dispos. 2006, 34(9):1582-1599.
Lang et al., "Mutations and polymorphisms in the bile salt export pump and the multidrug resistance protein 3 associated with drug-induced liver injury," Pharmacogenet Genomics, 2007, 17(1):47-60.
Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.
Lee et al., "Early Diagnosis of ABCB11 Spectrum Liver Disorders by Next Generation Sequencing," Pediatr Gastroenterol Hepatol Nutr. 2017, 20(2):114-123.
Lewis et al., "Effects of 2164U90 on ileal bile acid adsorption and serum cholesterol in rats and mice", Journal of Lipid Research 36(5):1098-1105, 1995.
Li et al., "ATP8B1 and ABCB 11 mutations in Chinese patients with normal gamma-glutamyl transferase cholestasis: Phenotypic differences between progressive familial intrahepatic cholestasis type 1 and 2," Hepatology International 2017, 11(1):5180. Abstract No. OP284.
Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China. Feb. 15, 2017-Feb. 19, 2017.
Li et al., "Effect of Resistant Starch Film Properties on the Colon-Targeting Release of Drug From Coated Pellets", 152 J Control. Rel. e5, 2011.
Lichtinghagen R, et al., "The Enhanced Liver Fibrosis (ELF) score: normal values, influence factors and proposed cut-off values," J Hepatol. Aug. 2013;59(2):236-42.
Lin et al., "Clinical and genetic analysis of an infant with progressive familial intrahepatic cholestasis type II].," Zhongguo Dang Dai Er Ke Za Zhi. 2018, 20(9)758-764 (with English abstract).
Ling, "Congenital cholestatic syndromes: What happens when children grow up?," Can J Gastroenterol, Nov. 11, 2007, 21(11):743-751.
Liu et al., "ABCB11 gene mutations in Chinese children with progressive intrahepatic cholestasis and low gamma glutamyltransferase," Liver International 2010, 30(6):809-815.
Liu et al., "Association of variants of ABCB11 with transient neonatal cholestasis," Pediatr Int. 2013, 55(2):138-144.
Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.
Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver, Hong Kong, China. Feb. 13, 2009-Feb. 16, 2009.
Liu et al., "Homozygous p.Ser267Phe in SLC10A1 is associated with a new type of hypercholanemia and implications for personalized medicine," Scientific Reports, 2017, 7(9214):1-7.
Liu, et al., "Patient-centered pharmaceutical design to improve acceptability of medicines: similarities and differences in paediatric and geriatric populations," Drugs 2014, 74(16):1871-1889.
Loh et al., "Overview of milling techniques for improving the solubility of poorly water-soluble drugs," Asian J Pharm Sci., 2015, 10:225-274.
Longo et al., "Hyperlipidemia in chronic cholestatic liver disease," Curr. Treat. Options Gastrenterol., 2001, 4:111-114.
Lopez et al., "Effect of formulation variables on oral grittiness and preferences of multiparticulate formulations in adult volunteers," Eur. J. Pharm. Sci. 2016, 92:156-162.
Lopez et al., "Formulation approaches to pediatric oral drug delivery: benefits and limitations of current platforms," Expert Opin. Drug Deliv., 2015, 12(11):1727-1740.
Lumena Pharmaceuticals Now Dosing Patients in the INDIGO Phase 2 Clinical Trial of LUM001 in Pediatric Patients with Progressive Familial Intrahepatic Cholestasis, PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
Lv et al., "Noninvasive Quantitative Detection Methods of Liver Fat Content in Nonalcoholic Fatty Liver Disease," J Clin Transl Hepatol. 2018, 6(2):217-221.
Lykavieris et al., "Outcome of liver disease in children with Alagille syndrome: a study of 163 patients," Gut, 2001, 49:431-435.
Maggiore et al., "Relapsing features of bile salt export pump deficiency after liver transplantation in two patients with progressive familial intrahepatic cholestasis type 2," J Hepatol. 2010, 53(5):981-6.
Manghat and Wierzbicki, "Colesevelam hydrochloride: a specifically engineered bile acid sequestrant," Future Lipidology, 3(3):237-255, Jun. 2008.
Marzorati et al., "A novel hypromellose capsule, with acid resistance properties, permits the targeted delivery of acid-sensitive products to the intestine," LWT-Food Sci. Techno.12015, vol. 60, p. 544-551.
Masahata et al., "Recurrence of Progressive Familial Intrahepatic Cholestasis Type 2 Phenotype After Living-donor Liver Transplantation: A Case Report," Transplant Proc. 2016, 48(9):3156-3162.
Massei et al., "Cholestasis as a presenting feature of acute epstein-barr virus infection," The pediatric Infectious Disease J., Feb. 2001, 5 pages.
Matte et al., "Analysis of gene mutations in children with cholestasis of undefined etiology," J Pediatr Gastroenterol Nutr. 2010, 51(4):488-493.
McCullough et al., "The epidemiology and risk factors of NASH.", Blackwell Publishing, Chapter 3, 2005.
McKay et al., "Mutation detection in cholestatic patients using microarray resequncing of ATP8B1 and ABCB11 [version 2; peer review: 2 approved, 1 approved with reservations]," F1000 Res., 2013, 2:32.
McMichael and Potter, "Reproduction, endogenous and exogenous sex hormones, and colon cancer: a review and hypothesis," J. Natl. Cancer Inst, 65(6):1201-07, Dec. 1980.
McPherson et al., "Simple non-invasive fibrosis scoring systems can reliably exclude advanced fibrosis in patients with non-alcoholic fatty liver disease," Gut 2010, 59(9):1265-9.
MerckManuals.com', "Obesity," 2008, Merch Manual for Health Care Professionals, Section—Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Michielsen et al., "Viral hepatitis and hepatocellular carcinoma," World Journal of Surg. Oncol, May 2005, 3(27):1-18.
Miloh et al., Gastroenterology, Meeting Info.: Digestive Disease Week Meeting/107th Annual Meeting of the American-GastroenterologicalAssociation. Los Angeles, CA, USA. May 2006, 130:(4)(2): A759-A760.
Minekus et al., "A computer-controlled system to simulate conditions of the large intestine with peristaltic mixing, water absorption and absorption of fermentation products," Appl. Microbiol Biatechnol. 1999, 53(1): 108-114.
Mishra et al., "Investigation of organoleptic characteristics in the development of soft chews of calcium carbonate as mineral supplement," Yakugaku Zasshi 2009, 129(12):1537-1544.
Mistry et al., "Evidence of acceptability of oral paediatric medicines: a review," J. Pharm. Pharmacol. 2017, 69(4):361-376.
Mizuochi et al., "Characterization of urinary bile acids in a pediatric BRIC-1 patient: effect of rifampicin treatment," Clin Chim Acta. 2012, 413(15-16):1301-1304.

(56) References Cited

OTHER PUBLICATIONS

Moghadamrad et al., "Cholestasis in a patient with gallstones and a normal gamma-glutamyl transferase," Hepatology, 2013, 57(6):2539-2541.
Molly et al., "Development of a 5-step multi-chamber reactor as a simulation of the human intestinal microbial system," Appl. Microbiol. Biatechnol. 1993, 39:254-258.
Morissette et al., "High-throughput crystallization: polymorphs, salts, co-crystals and solvates of pharmaceutical solids," Advanced Drug Delivery Reviews, 2004, 56:275-300.
Morotti et al., "Progressive Familial Intrahepatic Cholestasis (PFIC) Type 1, 2, and 3: A Review of the Liver Pathology Findings," Seminars in Liver Disease, Feb. 2011, 31(1):3-10.
Mouzaki and Allard, "Non-alcoholic steatohepatitis: the therapeutic challenge of a global epidemic," Annals of Gastroenterology, 2012, 25: 207-217.
Mowat et al., "Respiratory chain complex III [correction of complex] in deficiency with pruritus: a novel vitamin responsive clinical feature," J. Pediatr., 134(3):352-4, Mar. 1999.
Mwesigwa et al., "An investigation into moisture barrier film coating efficacy and its revelance to drug stability in solid dosage forms," Int. J. of Pharmacies, Jan. 2016, 497:70-77.
Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.
Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Narchi et al., "Intrahepatic cholestasis in two omani siblings associated with a novel homozygous ATP8B1 mutation, c.379C>G (p.L127V).," Saudi J Gastroenterol, 2017, 23(5):303-305.
Neuman, et al., "Biomarkers in nonalcoholic fatty liver disease," Can. J. Gastroenterol. Hepatol. 2014, 28(11):607-618.
Neuvonen et al., "Activated charcoal in the treatment of hypercholesterolaemia: dose-response relationships and comparison with cholestyramine," Eur J Clin Pharnnacol, 1989, 37(3):225.
Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.
Noe et al., "Impaired expression and function of the bile salt export pump due to three novel ABCB11 mutations in intrahepatic cholestasis," J Hepatol. 2005, 43(3):536-543.
O'Neill et al., "Comparison of efficacy of plant stanol ester and sterol ester: short-term and longer-term studies," American Journal of Cardiology, 96(1A):29d-36D, Jul. 2005.
Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.
Open Label Study to Evaluate Efficacy and Long Term Safety of LUM001 in the Treatment of Cholestatic Liver Disease in Patients With Progressive Familial Intrahepatic Cholestasis (INDIGO), Clinical Trials.gov, Feb. 5, 2014, retrieved on Oct. 3, 2014, http://clinicaltrials.gov/ct2/show/NCT02057718?term=LUM001&rank=4, 3 pages.
Open Label Study to Evaluate Safety and Efficacy of LUM001 in Patients With Primary Sclerosing Cholangitis (CAMEO), Clinical Trials.gov, Feb. 11, 2014, retrieved Oct. 3, 2014, http://clinicaltrials.gov/ct2/show/NCT02061540?term=LUM001&rank=6, 3 pages.
Pai et al. Compression and evaluation of extended release matrix pellets prepared by the extrusion/spheronization process into disintegrating tablets. Brazilian Journal of Pharmaceutical Sciences, vol. 48, n. 1, janinnar., 2012 (Year: 2012).

Painter et al., "Sequence variation in the ATP8B1 gene and intrahepatic cholestasis of pregnancy," Eur J Hum Genet. 2005, 13(4):435-439.
Park et al., "Clinical and ABCB11 profiles in Korean infants with progressive familial intrahepatic cholestasis," World J Gastroenterol., 2016, 22(20):4901-4907.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.
Pattni and Walters, "Recent advances in the understanding of bile acid malabsorption," Br. Med. Bull. 2009, vol. 92, p. 79-93.
Pauli-Magnus et al., "Enterohepatic transport of bile salts and genetics of cholestasis," Journal of Hepatology, 2005, 43(2):342-357.
Pauli-Magnus et al., "Impaired expression and function of the bile salt export pump due to three novel ABCB11 mutations in intrahepatic cholestasis," Hepatology 2003, vol. 38, No. 4 Suppl. 1, p. 518A. print. Meeting Info.: 54th Annual Meeting of the American Association for the Study of Liver Diseases. Boston, MA, USA. Oct. 24-28, 2003. American Association for the Study of Liver Diseases.
PCT International Search Report and Written Opinion in Application No. PCT/SE2019/050208, dated Jul. 8, 2019, 15 pages.
PCT International Search Report and Written Opinion in International Appln No. PCT/EP2020/084569, dated Mar. 9, 2021, 13 pages.
PCT International Search Report and Written Opinion in International Appln. No. PCT/EP2020/084567, dated Feb. 11, 2021, 13 pages.
PCT International Search Report and Written Opinion in International Appln. No. PCT/EP2020/084568, dated Feb. 11, 2021, 13 pages.
PCT International Search Report and Written Opinion in International Appln. No. PCT/EP2020/084570, dated Feb. 11, 2021, 13 pages.
PCT International Search Report and Written Opinion in International Appln. No. PCT/EP2020/084571, dated Feb. 4, 2021, 14 pages.
Peng et al., "[Relationship between phenotype and genotype of ABCB11 deficiency in siblings and literature review].," Zhonghua er ke za zhi (Chinese journal of pediatrics) 2018, 56(6):440-444.
Perez et al., "Bile-acid-induced cell injury and protection," World J Gastroenterol, Apr. 2009, 15(14)1677-1689.
Perumpail et al., "Clinical epidemiology and disease burden of nonalcoholic fatty liver disease," World Journal of Gastroenterology, Dec. 2017, 23(47): 8263-8276.
Phase 2 Study to Evaluate LUM001 in Combination With Ursodeoxycholic Acid in Patients With Primary Biliary Cirrhosis (CLARITY), Clinical Trials.gov, Jul. 17, 2013, retrieved Oct. 3, 2014, http://clinicaltrials.gov/ct2/show/NCT01904058?term=LUM001&rank=8, 3 pages.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Possemiers et al., "PCR-DGGE-based quantification of stability of the microbial community in a simulator of the human intestinal microbial ecosystem," FEMS Microbiol. Ecol. 2004, vol. 49, p. 495-507.
Poupon et al., "Chronic Cholestatic Disease," J. Hepatology, 2000, 32(1):12-140.
Progressive familial intrahepatic cholestasis, Wikipedia, the free encyclopedia, posted on or about Feb. 24, 2006, http://en.wikipedia.org/wiki/Progressive_familial_intrahepatic_cholestasis, 3 pages.
Qiu et al., "Defects in myosin VB are associated with a spectrum of previously undiagnosed low γ-glutamyltransferase cholestasis," Hepatology 2017, 65(5)1655-1669.
Qiu et al., "Disruption of BSEP function in HepaRG cells alters bile acid disposition and is a susceptive factor to drug-induced cholestatic injury," Mol. Pharmaceutics, 13:4,, 2016 (Abstract only).
Rancaniello, "How many viruses on earth?" Virology Blog, Sep. 2013, 6 pages.

(56) References Cited

OTHER PUBLICATIONS

Reeder et al., "Quantitative assessment of liver fat with magnetic resonance imaging and spectroscopy," J Magn Reson Imaging. 2011, 34(4):729-749.
Renga et al., "Role of FXR in regulating bile acid homeostasis and relevance for human diseases," Curr. Drug. Targets Immune Endocr. Metabol. Disord., 5(3):289-303, Sep. 2005.
Report EC20082069.02.01 dated Feb. 2009, filed with appellant's letter of Apr. 26, 2011.
Report filed at oral proceedings before opposition division, GMS-CFEP-2007-20, "Filtration and Drying Study on Amorphous and Form IV Atorvastatin Calcium," 2007.
Ricci, "Bridging studies in support of oral pediatric formulation development," Int. J. Pharmaceuticals, 2013, 457:323-326.
Rolo et al., "Bile acids affect liver mitochondrial bioenergetics: Possible relevance for cholestasis therapy," Toxocological Sciences, 57: 177-185, 2000.
RU Office Action in Russian Appln. No. 2018131255, dated May 19, 2020, 16 pages (with English translation).
Rumbo et al., Transplantation 2018, vol. 102, No. 7, Supp. Supplement 1, pp. 5848. Abstract No. P.752. Meeting Info: 27th International Congress of The Transplantation Society, TTS 2018, Madrid, Spain, Jun. 30, 2018-Jul. 5, 2018.
Ryder, "Guidelines for the diagnosis and treatment of hepatocellular carcinoma (HCC) in adults," Gut, May 2003, 52:(Suppl.111):iii1-iii8.
Safety and Efficacy Study of LUM001 in the Treatment of Cholestatic Liver Disease in Patients With Alagille Syndrome (IMAGO), Clinical Trials.gov, Jul. 16, 2013, http://clinicaltrials.gov/ct2/show/NCT01903460?term=LUM001&rank=1, 3 pages.
Sanyal et al. The etiology of hepatocellular carcinonna and consequences of treatment. The Oncologist, 2010, 15 Suppl 4, 14-22.
Satapathy and Sanyal, "Epidemiology and Natural History of Non-alcoholic Fatty Liver Disease," Seminars in Liver Disease, Aug. 2015, 35(3): 221-235.
Sattler et al., "Functional analysis of previously uncharacterised disease-causing mutations of the bile salt export pump," Journal of Hepatology 2017, 66(1):5177. Meeting Info.: International Liver Congress/ 52nd Annual Meeting of the European-Association-for-the-Studyof-the-Liver. Amsterdam, Netherlands. Apr. 19-23, 2017, European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-GastroenterologicalAssociation. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Scheuer, "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Schumpelick et al., "[Ulcerative colitis—late functional results of ileoanal pouch anastomosis]," Chirung, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):S329. Abstract No. CO18, Meeting Info: 17th National Congress SIGENP. Pescara, Italy. Oct. 7, 2010-Oct. 9, 2010.
SE Search Report in Swedish Appln. No. 1850474-6, dated Oct. 11, 2018, 3 pages.
Shah et al., "Progressive Familial Intrahepatic Cholestasis Type 2 in an Indian Child," J Pediatr Genet. 2017, 6(2):126-127.
Shah et al., "Role of Caco-2 Cell Monolayers in Prediction of Intestinal Drug Absotrption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017. Bhubaneswar, India. Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Singhal et al., "Drug polymorphism and dosage form design: a practical perspective," Adv Drug Deliv Rev, Feb. 23, 2004, 56(3):335-347.
Sinha and Kumria, "Microbially triggered drug delivery to the colon," Eur. J. Pharm. Sci. 2003, vol. 18, p. 3-18.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile acid sequestrants and the treatment of type 2 diabetes mellitus," Drugs, 67(10):1383-92, 2007.
Stein, "Managing Dyslipidemia in the High-Risk Patient," Am J. Cardiol., 2002, 89:50-57.
Sterling et al., "Steatohepatitis: Risk factors and impact on disease severity in human immunodeficiency virus/hepatitis c virus coinfection," Hepatology, Apr. 2008, 47(4) 1118-1127.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology. 2008, 134(4):1203-1214.
Sun et al., "Bile acids promote diethylnitrosamine-induced hepatocellular carcinoma via increased inflammatory signaling," American Journal of Physiology—Gastrointestinal and Liver Physiology, May 5, 2016, 311(1):G91-104.
Sutyagin et al., Chemistry and Physics of Polymers: Textbook. -Tomsk: TPU Publishing House, 2003, p. 132, 140-143, 151-152, 173-174 (machine translation).
Suzuki and Takada, "Mechanisms of regulation of bile acid transport in the small intestine," Falk Symposium, 165:76-81, 2009.

(56) References Cited

OTHER PUBLICATIONS

Swedish Office Action for Swedish Appln. No. 1850915-8, dated Feb. 15, 2019, 6 pages.
Swedish Office Action in SW Appln. No. 1950463-8, dated Sep. 26, 2019, 3 pages.
Swedish Office Action in SW Appln. No. 1950464-6, dated Sep. 26, 2019, 3 pages.
Swedish Office Action in Swedish Appln. No. 1850761-6, dated Dec. 17, 2018, 8 pages.
Swedish Office Action in Swedish Appln. No. 1850762-4, dated Dec. 27, 2018, 7 pages.
Swedish Search Report for Swedish Appln. No. 1850915-8, dated Feb. 15, 2019, 2 pages.
Swedish Search Report in SW Appln. No. 1950463-8, dated Sep. 26, 2019, 2 pages.
Swedish Search Report in SW Appln. No. 1950464-6, dated Sep. 26, 2019, 3 pages.
Swedish Search Report in Swedish Appln. No. 1850761-6, dated Dec. 17, 2018, 3 pages.
Swedish Search Report in Swedish Appln. No. 1850762-4, dated Dec. 27, 2018, 3 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Biliary Cirrhosis," Am. J. Gastroenterology, 2001, 96(1): 8-15.
Thakral et al., "Eudragit: a technology evaluation," Expert Opin. Drug Deliv., Jan. 2013, 10(1):131-149.
Tian et al., "Factors affecting crystallization of hydrates," J. Pharm. Pharmacol., 2010, 62:1534-1546.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in Japanese patients with intrahepatic cholestasis associated with low gamma-glutamyl transpeptidase level," Journal of Pediatric Gastroenterology and Nutrition 2018, 67(1):S363, Abstract No. 615.
Tollefson et al., "A novel class of apical sodium co-dependent bile acid transporter inhibitors: the 1,2-Benzothiazepines", Bioorganic and Medicinal Chemistry Letters 12:3727-3730, 2003.
Trauner et al., "Inflammation-induced cholestasis," J. of Gastroenterology and Hepatology, Dec. 2001, 14:10:946-959.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codependent Bile Acid Transporter Inhibitors (Part 1)," J. Med. Chem, 2005, 48:5837-5852.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology, 2004, 127(2):379-384.
Van Tilberg et al., "Na+-dependent bile acid transport in the ileum: the balance between diarrhea and constipation", Gastroenterology 98(1):25-32, 1989.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food Nutr. Sci., 58(4):401-405, 2008.
Walsh et al., "Patient acceptability, safety and access: A balancing act for selecting age-appropriate oral dosage forms for paediatric and geriatric populations," Int. J. Pharm, 2017, 536(2):547-562.
Walsh et al., "Respiratory syncytial and other virus infections in persons with chronic cardiopulmonary disease," American Journal of Respiratory Critical Care Med., 1999, 160:791-795.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Wang et al.,"Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; H(4):e0153114.
Watts and Illum, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.
What is Alagille Syndrome?, European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Whitington et al., "Partial external diversion of bile for the treatment of intractable pruritus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.

(56) References Cited

OTHER PUBLICATIONS

Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.
Zhang et al., "Abcb11 deficiency induces cholestasis coupled to impaired B-Fatty acid oxidation in mice," Journal of biological chemistiy, 287: 29, 24784-2479, 2012.
Zhang et al., "Effect of bile duct ligation on bile acid composition in mouse serum and liver," Liver int, 32: 1, 58-69, 2012.
Al-Dury, "Ileal Bile Acid Transporter Inhibition for the Treatment of Chronic Constipation, Cholestatic Pruritus, and NASH," Fromtiers in Pharmacology, 2018, 9:931.
International Search Report and Written Opinion in Appl. No. PCT/EP2021/081462, dated Jan. 1, 2022, 18 pages.
Sangkhathat et al., "Variants Associated with Infantile Cholestatic Syndromes Detected in Extrahepatic Biliary Atresia by Whole Exome Studies: A 20-Case Series from Thailand," J. Pediatr Genet., 2018, 7:67-73.
Slavetinsky et al., "Odevixibat and partial external biliary diversion showed equal improvement of cholestasis in a patient with progressive familial intrahepatic cholestasis," BMJ Case Rep, 2020, 13:e234185.
[No Author]"EASL Clinical Practice Guidelines: management of cholestatic liver diseases," J. Hepatol., Aug. 2009, 51:2:237-67.
Baker et al. "Systematic review of progressive familial intrahepatic cholestasis," Clin Res Hepatol Gastroenterol., 2019;43:20-36.
Bull et al., "Progressive Familial Intrahepatic Cholestasis," Clin Liver Dis., Nov. 2018, 22:4:657-669.
Clinical Trials Identifier: NCT03566238, "A Double-Blind, Randomized, Placebo-Controlled, Phase 3 Study to Demonstrate Efficacy and Safety of A4250 in Children With Progressive Familial Intrahepatic Cholestasis Types 1 and 2 (PEDFIC 1)," version 24, Apr. 18, 2019, 8 pages.
Clinical Trials Identifier: NCT03659916, "Long Term Safety & Efficacy Study Evaluating The Effect of A4250 in Children With PFIC," version 11, Oct. 24, 2019, 7 pages.
Fujino et al., "Pruritus in patients with chronic liver disease and serum autotaxin levels in patients with primary biliary cholangitis," BMC Gastro., 2019, 19:169.
Gillberg et al., "Clinical Pharmacology of odevixibat, a potent, selective ileal bile acid transport inhibitor with minimal systemic exposure," Annual Meeting A4250: Naspghan, J Pediatr Gastroenterol Nutr., 69(suppl 2):S113 Abstract No. 166-167, 2019.
Kamath et al, "Potential of ileal bile acid transporter inhibition as a therapeutic target in Alagille syndrome and progressive familial intrahepatic cholestasis," Liver int., Aug. 2020, 40:8:1812-1822.
Kremer et al., "Serum autotaxin is increased in pruritus of cholestasis, but not of other origin, and responds to therapeutic interventions," Hepatology, Oct. 2012, 56:4:1391-400.

Thebaut et al., "An update on the physiopathology and therapeutic management of cholestatic pruritus in children," Clinics and Res in Hepatology and Gastro., 2018, 42:2:103-109.
Van Wessel et al., "Genotype correlates with the natural history of severe bile salt export pump deficiency," Multicenter Study., Jul. 2020, 73:1:84-93.
Almasio et al., "Role of S-adenosyl-L-methionine in the treatment of intrahepatic cholestasis," Drugs, 1990, 40 Suppl (3):111-123.
Asami et al., "Treatment of children with familial hypercholesterolemia with colestilan, a newly developed bile acid-binding resin," Atherosclerosis, 2002, 164:381-2.
Baringhaus, "Substrate specificity of the ileal and the hepatic Na+/bile acid cotransporters of the rabbit. II. A reliable 3D QSAR pharmacophore model for the ileal Na+/bile acid cotransporter," J. Lipid Res., 1999, 40:2158-2168.
Bass et al., "Inherited Disorders of Cholestasis in Adulthood," Clin. Liver. Dis., 2013, 2(5):200-203.
Charach et al., "The association of bile acid excretion and atherosclerotic coronary artery disease," Therapeutic Advances in Gastroenterology, 2011, 4(2):95-101.
Ellis et al. "Feedback regulation of human bile acid synthesis," Falk Symposium, 2005, 141:73-79.
Farmer et al., "Currently available hypolipidaemic drugs and future therapeutic developments," Baillieres Clin Endocrinol Metab, 1995, 9(4):825-47.
Glueck, "Colestipol and probucol: treatment of primary and familial hypercholesterolemia and amelioration of atherosclerosis," Ann. Intern. Med, Apr. 1982, 96(4): 475-82.
Guo et al., "Serum Metabolomic Analysis of Coronary Heart Disease Patients with Stable Angina Pectoris Subtyped by Traditional Chinese Medicine Diagnostics Reveals Biomarkers Relevant to Personalized Treatments," Frontiers in Pharmacology, Jun. 2022, 12:1-14.
Hofmann, "Defective Biliary Secretion during Total Parenteral Nutrition," J. Ped. Gastro, & Nutr, May 1995, 20(4):376-390.
Khurana et al., "Bile Acids Regulate Cardiovascular Function," Clin Transl Sci, Jun. 2011, 4(3):210-218.
Mehl et al. "Liver transplantation and the management of progressive familial intrahepatic cholestasis in children," World J. Transplant, 2016, 6(2):278-90.
Parikh et al., "Batch Fluid Bed Granulation," Handbook of Pharmaceutical Granulation Technology, 2010, pp. 204-260.
PCT International Search Report and Written Opinion in International Application No. PCT/EP2021/084081, dated Jan. 27, 2022, 13 pages.
PCT International Search Report and Written Opinion in International Application No. PCT/EP2022/065165, dated Aug. 23, 2022, 9 pages.
Schonherr, "Profound Methyl Effects in Drug Discovery and a Call for New C—H Methylation Reactions," Angew. Chem. Int. Ed., 2013, 52:12256-12267.
Vasavan et al., "Heart and bile acids—Clinical consequences of altered bile acid metabolism," BBA—Molecular Basis of Disease, 2018, 1864:1345-1355.

\* cited by examiner

IBAT INHIBITORS FOR THE TREATMENT OF LIVER DISEASES

CROSS-REFERENCE TO RELATED APPLICATIONS

This application is a continuation of U.S. patent application Ser. No. 16/737,742, filed Jan. 8, 2020, which is a continuation of U.S. patent application Ser. No. 15/069,199, filed Mar. 14, 2016, which is a continuation of U.S. patent application Ser. No. 13/881,447, filed May 17, 2013, which is a National Stage application under 35 U.S.C. § 371 of International Application No. PCT/SE2011/051335, filed Nov. 8, 2011, which claims the benefit of U.S. Patent Application No. 61/410,957, filed Nov. 8, 2010, and Swedish Patent Application No. 1051165-7, filed Nov. 8, 2010, all of which are incorporated by reference in their entirety.

BACKGROUND OF THE INVENTION

Ileal bile acid transporter (IBAT) is the main mechanism for re-absorption of bile acids from the GI tract. Partial or full blockade of that mechanism will result in lower concentration of bile acids in the small bowel wall, portal vein, liver parenchyma, intrahepatic biliary tree, extrahepatic biliary tree, including gall bladder.

Diseases which may benefit from partial or full blockade of the IBAT mechanism may be those either having as a primary pathophysiological defect, causing or having symptoms of too high concentration of bile acids in serum and in the above organs. WO 2008/058630 describes the effect of certain ileal bile acid transport (IBAT) in the treatment of liver disease related to fat disorders.

SUMMARY OF THE INVENTION

The present invention regards specific IBAT inhibitors in the prophylaxis and/or treatment of a liver disease.

DETAILED DESCRIPTION OF THE INVENTION

The invention relates to IBAT inhibitory compounds of formula (I):

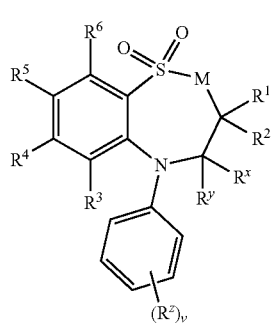

(I)

wherein:
M is $CH_2$, NH
One of $R^1$ and $R^2$ are selected from hydrogen or $C_{1-6}$alkyl and the other is selected from $C_{1-6}$alkyl;
$R^x$ and $R^y$ are independently selected from hydrogen, hydroxy, amino, mercapto, $C_{1-6}$alkyl, $C_{1-6}$alkoxy,

{{RIGHT COLUMN}}

N—($C_{1-6}$alkyl)amino, N,N—($C_{1-6}$alkyl)$_2$amino, $C_{1-6}$alkylS(O)$_a$ wherein a is 0 to 2
$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
v is 0-5;
one of $R^4$ and $R^5$ is a group of formula (IA):

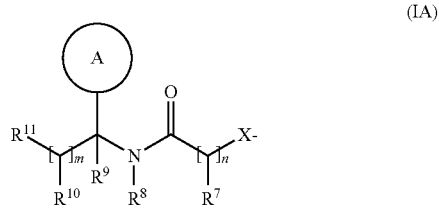

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{16}$;
X is —O—, —N($R^a$)—, —S(O)$_b$— or —CH($R^a$)—; wherein $R^a$ is hydrogen or $C_{1-6}$alkyl and b is 0-2;
Ring A is aryl or heteroaryl; wherein Ring A is optionally substituted by one or more substituents selected from $R^{17}$;
$R^7$ is hydrogen, $C_{1-4}$alkyl, carbocyclyl or heterocyclyl; wherein $R^7$ is optionally substituted by one or more substituents selected from $R^{18}$;
$R^8$ is hydrogen or $C_{1-4}$alkyl;
$R^9$ is hydrogen or $C_{1-4}$alkyl;
$R^{10}$ is hydrogen, $C_{1-4}$alkyl, carbocyclyl or heterocyclyl; wherein $R^{10}$ is optionally substituted by one or more substituents selected from $R^{19}$;
$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or $R^{11}$ is a group of formula (IB) or (IC):
wherein:

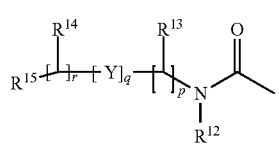

(IB)

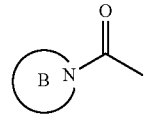

(IC)

Y is —N(R")—, —N(R")C(O)—, —N(R")C(O)(CR$^s$R$^t$)$_v$N(R")C(O)—, —O—, and —S(O)a-; wherein a is 0-2, v is 1-2, R$^s$ and R$^t$ are independently selected from hydrogen or C$_{1-4}$alkyl optionally substituted by R$^{26}$ and R" is hydrogen or C$_{1-4}$alkyl;

R$^{12}$ is hydrogen or C$_{1-4}$alkyl;

R$^{13}$ and R$^{14}$ are independently selected from hydrogen, C$_{1-4}$alkyl, carbocyclyl or heterocyclyl; and when q is 0, R$^{14}$ may additionally be selected from hydroxy wherein R$^{13}$ and R$^{14}$ may be independently optionally substituted by one or more substituents selected from R$^{20}$;

R$^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from C$_{1-6}$alkyl;

p is 1-3; wherein the values of R$^{13}$ may be the same or different;

q is 0-1;

r is 0-3; wherein the values of R$^{14}$ may be the same or different;

m is 0-2; wherein the values of R$^{10}$ may be the same or different;

n is 1-3; wherein the values of R$^7$ may be the same or different;

Ring B is a nitrogen linked heterocyclyl substituted on carbon by one group selected from R$^{23}$, and optionally additionally substituted on carbon by one or more R$^{24}$; and wherein if said nitrogen linked heterocyclyl contains an —NH— moiety, that nitrogen may be optionally substituted by a group selected from R$^{25}$;

R$^{16}$, R$^{17}$ and R$^{18}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl; wherein R$^{16}$, R$^{17}$ and R$^{18}$ may be independently optionally substituted on carbon by one or more R$^2$;

R$^{19}$, R$^{20}$, R$^{24}$ and R$^{26}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl, N,N—(C$_{1-4}$alkyl)$_2$sulphamoyl, carbocyclyl, heterocyclyl, benzyloxycarbonylamino, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from C$_{1-6}$alkyl; wherein R$^{19}$, R$^{20}$, R$^{24}$ and R$^{26}$ may be independently optionally substituted on carbon by one or more R$^{22}$ R$^{21}$ and R$^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

R$^{23}$ is carboxy, sulpho, sulphino, phosphono, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from C$_{1-6}$alkyl;

R$^{25}$ is selected from C$_{1-6}$alkyl, C$_{1-6}$alkanoyl, C$_{1-6}$alkylsulphonyl, C$_{1-6}$alkoxycarbonyl, carbamoyl, N—(C$_{1-6}$alkyl)carbamoyl, N,N—(C$_{1-6}$alkyl)carbamoyl, benzyl, benzyloxycarbonyl, benzoyl and phenylsulphonyl;

or a pharmaceutically acceptable salt, solvate, solvate of such a salt or a prodrug thereof for use in the prophylaxis or treatment of a liver disease.

Compounds as used in accordance with the invention improve liver tests (serum amino transferases) and liver histology and significantly reduce hydroxyproline content and the number of infiltrating neutrophils and proliferating hepatocytes and cholangiocytes.

In the literature IBAT inhibitors are often referred to by different names. It is to be understood that where IBAT inhibitors are referred to herein, this term also encompasses compounds known in the literature as: i) ileal apical sodium co-dependent bile acid transporter (ASBT) inhibitors; ii) bile acid transporter (BAT) inhibitors; iii) ileal sodium/bile acid cotransporter system inhibitors; iv) apical sodium-bile acid cotransporter inhibitors; v) ileal sodium-dependent bile acid transport inhibitors; vi) bile acid reabsorption (BARI's) inhibitors; and vii) sodium bile acid transporter (SBAT) inhibitors; where they act by inhibition of IBAT.

In this specification the term "alkyl" includes both straight and branched chain alkyl groups but references to individual alkyl groups such as "propyl" are specific for the straight chain version only. For example, "C$_{1-6}$alkyl" includes C$_{1-4}$alkyl, C$_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenylC$_{1-6}$alkyl" would include phenylC$_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"Heteroaryl" is a totally unsaturated, mono or bicyclic ring containing 3-12 atoms of which at least one atom is chosen from nitrogen, sulphur or oxygen, which may, unless otherwise specified, be carbon or nitrogen linked. Preferably "heteroaryl" refers to a totally unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked. In another aspect of the invention, "heteroaryl" refers to a totally unsaturated, monocyclic ring containing 5 or 6 atoms or a bicyclic ring containing 8, 9 or 10 atoms of which at least one atom is chosen from nitrogen, sulphur or oxygen, which may, unless otherwise specified, be carbon or nitrogen linked. Examples and suitable values of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. Preferably the term "heteroaryl" refers to thienyl or indolyl.

"Aryl" is a totally unsaturated, mono or bicyclic carbon ring that contains 3-12 atoms. Preferably "aryl" is a monocyclic ring containing 5 or 6 atoms or a bicyclic ring containing 9 or atoms. Suitable values for "aryl" include phenyl or naphthyl. Particularly "aryl" is phenyl.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$-group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo [2.2.1] heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3-12 atoms; wherein a —CH$_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$alkanoyloxy" and "$C_{1-4}$alkanoyloxy" is acetoxy. Examples of "$C_{1-6}$alkoxycarbonyl" and "$C_{1-4}$alkoxycarbonyl" include methoxycarbonyl, ethoxycarbonyl, n- and t-butoxycarbonyl. Examples of "$C_{1-6}$alkoxy" and "$C_{1-4}$alkoxy" include methoxy, ethoxy and propoxy. Examples of "$C_{1-6}$alkanoylamino" and "$C_{1-4}$alkanoylamino" include formamido, acetamido and propionylamino. Examples of "$C_{1-6}$alkylS(O)$_a$ wherein a is 0 to 2" and "$C_{1-4}$ alkylS(O)$_a$ wherein a is 0 to 2" include methylthio, ethylthio, methylsulphinyl, ethylsulphinyl, mesyl and ethylsulphonyl. Examples of "$C_{1-6}$alkanoyl" and "$C_{1-4}$alkanoyl" include $C_{1-3}$alkanoyl, propionyl and acetyl. Examples of "N—($C_{1-6}$alkyl)amino" and "N—($C_{1-4}$alkyl)amino" include methylamino and ethylamino. Examples of "N,N—($C_{1-6}$alkyl)$_2$amino" and "N,N—($C_{1-4}$ alkyl)$_2$amino" include di-N-methylamino, di-(N-ethyl)amino and N-ethyl-N-methylamino. Examples of "$C_{2-6}$alkenyl" and "$C_{2-4}$alkenyl" are vinyl, allyl and 1-propenyl. Examples of "$C_{2-6}$alkynyl" and "$C_{2-4}$alkynyl" are ethynyl, 1-propynyl and 2-propynyl. Examples of "N—($C_{1-6}$ alkyl)sulphamoyl" and "N—($C_{1-4}$alkyl)sulphamoyl" are N—($C_{1-3}$alkyl)sulphamoyl, N-(methyl)sulphamoyl and N-(ethyl)sulphamoyl. Examples of "N—($C_{1-6}$alkyl)$_2$sulphamoyl" and "N-4alkyl)$_2$sulphamoyl" are N,N-(dimethyl)sulphamoyl and N-(methyl)-N-(ethyl)sulphamoyl. Examples of "N—($C_{1-6}$alkyl)carbamoyl" and "N—($C_{1-4}$alkyl)carbamoyl" are methylaminocarbonyl and ethylaminocarbonyl. Examples of "N,N—($C_{1-6}$alkyl)$_2$carbamoyl" and "N,N—($C_{1-4}$alkyl)$_2$-carbamoyl" are dimethylaminocarbonyl and methylethylaminocarbonyl. Examples of "$C_{1-6}$ alkoxycarbonylamino" are ethoxycarbonylamino and t-butoxycarbonylamino. Examples of "N'—($C_{1-6}$alkyl)ureido" are N'-methylureido and N'-ethylureido. Examples of "N—($C_{1-6}$alkyl)ureido are N-methylureido and N-ethylureido. Examples of "N',N'—($C_{1-6}$alkyl)$_2$ureido are N',N'-dimethylureido and N'-methyl-N'-ethylureido. Examples of "N'—($C_{1-6}$alkyl)-N—($C_{1-6}$alkyl)ureido are N'-methyl-N-methylureido and N'-propyl-N-methylureido. Examples of "N',N'—($C_{1-6}$alkyl)$_2$-N—($C_{1-6}$alkyl)ureido are N',N'-dimethyl-N-methylureido and N'-methyl-N'-ethyl-N-propylureido.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid.

In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

Compounds of formula (I) may be administered in the form of a pro-drug which is broken down in the human or animal body to give a compound of the formula (I).

Examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$ alkanoyloxymethyl esters for example pivaloyloxymethyl, phthalidyl esters, $C_{3-8}$ cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxy-carbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide. It is also to be understood that certain compounds of the formula (I) can exist in solvated as well as unsolvated forms such as, for example, hydrated forms. It is to be understood that the invention encompasses all such solvated forms which possess IBAT inhibitory activity.

Preferred values of $R^1$, $R^2$, $R^3$, $R^4$, $R^5$ and $R^6$ are as follows. Such values may be used where appropriate with any of the definitions, claims or embodiments defined hereinbefore or hereinafter.

Preferably $R^1$ and $R^2$ are independently selected from $C_{1-4}$alkyl.

More preferably $R^1$ and $R^2$ are independently selected from ethyl or butyl.

More preferably $R^1$ and $R^2$ are independently selected from ethyl, propyl or butyl.

In one aspect of the invention particularly $R^1$ and $R^2$ are both butyl.

In a further aspect of the invention particularly $R^1$ and $R^2$ are both propyl.

In another aspect of the invention particularly one of $R^1$ and $R^2$ is ethyl and the other is butyl.

Preferably $R^x$ and $R^Y$ are independently selected from hydrogen or $C_{1-6}$alkyl.

More preferably $R^x$ and $R^Y$ are both hydrogen.

Preferably $R^Z$ is selected from halo, amino, $C_{1-6}$alkyl, $C_{1-6}$alkoxycarbonylamino or N'—($C_{1-6}$alkyl)ureido.

More preferably $R^Z$ is selected from chloro, amino, t-butyl, t-butoxycarbonylamino or N'-(t-butyl)ureido.

Preferably v is 0 or 1.

In one aspect of the invention, more preferably v is 0.

In one aspect of the invention, more preferably v is 1.

In one aspect of the invention preferably $R^4$ is a group of formula (IA) (as depicted above). In another aspect of the invention preferably $R^5$ is a group of formula (IA) (as depicted above).

Preferably $R^3$ and $R^6$ are hydrogen.

Preferably the other of $R^4$ and $R^5$ that is not the group of formula (IA) is selected from halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy and N,N—($C_{1-4}$alkyl)$_2$amino.

More preferably the other of $R^4$ and $R^5$ that is not the group of formula (IA) is selected from bromo, methoxy, isopropoxy, methylthio, ethylthio, isopropylthio or mesyl; wherein that $R^4$ or $R^5$ may be optionally substituted on carbon by one or more $R^{16}$; wherein $R^{16}$ is independently selected from hydroxy and N,N-dimethylamino.

Particularly the other of $R^4$ and $R^5$ that is not the group of formula (IA) is selected from bromo, methoxy, isopropoxy, methylthio, ethylthio, isopropylthio, 2-hydroxyethylthio, 2-(N,N-dimethylamino) ethylthio or mesyl.

More particularly the other of $R^4$ and $R^5$ that is not the group of formula (IA) is methylthio. Preferably the other of $R^4$ and $R^5$ that is not the group of formula (IA) is selected from hydrogen, halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy, carboxy and N,N—($C_{1-4}$alkyl)$_2$amino.

More preferably the other of $R^4$ and $R^5$ that is not the group of formula (IA) is selected from hydrogen, bromo, methoxy, isopropoxy, methylthio, ethylthio, isopropylthio or mesyl; wherein that $R^4$ or $R^5$ may be optionally substituted on carbon by one or more $R^{16}$; wherein $R^{16}$ is independently selected from hydroxy, carboxy and N,N-dimethylamino.

Particularly the other of $R^4$ and $R^5$ that is not the group of formula (IA) is selected from hydrogen, bromo, methoxy, isopropoxy, methylthio, carboxymethylthio, ethylthio, isopropylthio, 2-hydroxyethylthio, 2-(N,N-dimethylamino) ethylthio or mesyl.

In another aspect of the invention, more preferably the other of $R^4$ and $R^5$ that is not the group of formula (IA) is selected from hydrogen, chloro, bromo, methoxy, isopropoxy, methylthio, ethylthio or isopropylthio; wherein that $R^4$ or $R^5$ may be optionally substituted on carbon by one or more $R^{16}$; wherein $R^{16}$ is independently selected from hydroxy, carboxy and N,N-dimethylamino.

In another aspect of the invention, particularly the other of $R^4$ and $R^5$ that is not the group of formula (IA) is selected from hydrogen, chloro, bromo, methoxy, isopropoxy, methylthio, carboxymethylthio, ethylthio, isopropylthio, 2-hydroxyethylthio or 2-(N,N-dimethylamino) ethylthio.

In another aspect of the invention, more particularly the other of $R^4$ and $R^5$ that is not the group of formula (IA) is bromo or chloro.

In another aspect of the invention, more particularly the other of $R^4$ and $R^5$ that is not the group of formula (IA) is methoxy.

In one aspect of the invention, preferably Ring A is aryl.

In another aspect of the invention, preferably Ring A is heteroaryl.

When Ring A is aryl, preferably Ring A is phenyl.

When Ring A is heteroaryl, preferably Ring A is thienyl or indolyl.

Preferably Ring A is aryl or heteroaryl; wherein Ring A is optionally substituted by one or more substituents selected from $R^{17}$; wherein $R^{17}$ is selected from halo, hydroxy or C1 4alkyl; wherein $R^{17}$ may be optionally substituted on carbon by one or more $R^{21}$; wherein $R^{21}$ is selected from halo.

Preferably X is —O.

More preferably Ring A is phenyl, thienyl or indolyl; wherein Ring A is optionally substituted by one or more substituents selected from halo, hydroxy or trifluoromethyl.

Particularly Ring A is selected from phenyl, 4-hydroxyphenyl, thien-2-yl, 4-trifluoromethylphenyl, 3-hydroxyphenyl, 2-fluorophenyl, 2,3-dihydroxyphenyl or indol-3-yl. More particularly Ring A is phenyl.

In another aspect of the invention, preferably Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo.

In another aspect of the invention, more preferably Ring A is phenyl, thienyl or indolyl; wherein Ring A is optionally substituted by one or more substituents selected from halo, hydroxy, methoxy or trifluoromethyl.

In another aspect of the invention, particularly Ring A is selected from phenyl, 4-hydroxyphenyl, 4-methoxyphenyl, thien-2-yl, 4-trifluoromethylphenyl, 3-hydroxyphenyl, 2-fluorophenyl, 2,3-dihydroxyphenyl or indol-3-yl.

In a further aspect of the invention, particularly Ring A is selected from phenyl, 4-hydroxyphenyl, 4-methoxyphenyl, thien-2-yl, 4-trifluoromethylphenyl, 3-hydroxyphenyl, 2-fluorophenyl, 4-fluorophenyl, 2,3-dihydroxyphenyl or indol-3-yl.

Preferably $R^7$ is hydrogen, $C_{1-4}$alkyl or carbocyclyl.
More preferably $R^7$ is hydrogen, methyl or phenyl.
Particularly $R^7$ is hydrogen.

In one aspect of the invention, preferably $R^8$ is hydrogen.
In another aspect of the invention, preferably $R^8$ is $C_{1-4}$alkyl.

In another aspect of the invention, more preferably $R^8$ is hydrogen or methyl.

In one aspect of the invention, preferably $R^9$ is hydrogen.
In another aspect of the invention, preferably $R^9$ is $C_{1-4}$alkyl.

In another aspect of the invention, more preferably $R^9$ is hydrogen or methyl.

Preferably $R^{10}$ is hydrogen.

In one aspect of the invention, preferably $R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl.

In another aspect of the invention, preferably $R^{11}$ is a group of formula (IB) (as depicted above).

Preferably $R^{11}$ is carboxy, —P(O)(OH)(OR$^c$) or a group of formula (IB) (as depicted above).

More preferably $R^{11}$ is carboxy, —P(O)(OH)(OEt) or a group of formula (IB) (as depicted above).

In another aspect of the invention, preferably $R^{11}$ is carboxy, sulpho, —P(O)(OH)(OR$^c$) wherein R$^c$ is selected from $C_{1-4}$alkyl or a group of formula (IB) (as depicted above).

Preferably Y is —NH— or —NHC(O)—.
More preferably Y is —NHC(O)—.

In one aspect of the invention, preferably $R^{12}$ is hydrogen.
In another aspect of the invention, preferably $R^{12}$ is $C_{1-4}$alkyl.

In another aspect of the invention, more preferably $R^{12}$ is hydrogen or methyl.

Preferably $R^{13}$ is hydrogen, $C_{1-4}$alkyl or carbocyclyl; wherein $R^{13}$ is optionally substituted by one or more substituents selected from $R^{20}$; wherein $R^{20}$ is hydroxy.

More preferably $R^{13}$ is hydrogen, methyl or phenyl; wherein $R^{13}$ is optionally substituted by one or more substituents selected from $R^{20}$; wherein $R^{20}$ is hydroxy.

Particularly $R^{13}$ is hydrogen, hydroxymethyl or phenyl.
More particularly $R^{13}$ is hydrogen or hydroxymethyl.

In another aspect of the invention, preferably $R^{13}$ is hydrogen, $C_{1-4}$alkyl or carbocyclyl; wherein $R^{13}$ is optionally substituted by one or more substituents selected from $R^{20}$; wherein $R^{20}$ is hydroxy, carboxy, carbocyclyl or amino; wherein $R^{20}$ may be optionally substituted on carbon by one or more $R^{22}$; $R^{22}$ is hydroxy.

In another aspect of the invention, more preferably $R^{13}$ is hydrogen, methyl, ethyl, butyl or phenyl; wherein $R^{13}$ is optionally substituted by one or more substituents selected from $R^{20}$; wherein $R^{20}$ is hydroxy, carboxy, phenyl or amino; wherein $R^{20}$ may be optionally substituted on carbon by one or more $R^{22}$; $R^{22}$ is hydroxy.

In another aspect of the invention, particularly $R^{13}$ is hydrogen, hydroxymethyl, 4-aminobutyl, 2-carboxyethyl, 4-hydroxybenzyl or phenyl.

In a further aspect of the invention, preferably $R^{13}$ is hydrogen, $C_{1-4}$alkyl or carbocyclyl; wherein $R^{13}$ is optionally substituted by one or more substituents selected from $R^{20}$; wherein $R^{20}$ is hydroxy, carboxy, carbocyclyl, heterocyclyl or amino; wherein $R^{20}$ may be optionally substituted on carbon by one or more $R^{22}$; $R^{22}$ is hydroxy.

In a further aspect of the invention, more preferably $R^{13}$ is hydrogen, methyl, ethyl, butyl or phenyl; wherein $R^{13}$ is optionally substituted by one or more substituents selected from $R^{20}$; wherein $R^{20}$ is hydroxy, carboxy, phenyl, imidazolyl or amino; wherein $R^{20}$ may be optionally substituted on carbon by one or more $R^{22}$; $R^{22}$ is hydroxy.

In a further aspect of the invention, particularly $R^{13}$ is hydrogen, hydroxymethyl, 4-aminobutyl, 2-carboxyethyl, 4-hydroxybenzyl, imidazol-5-ylmethyl or phenyl.

In another further aspect of the invention, preferably $R^{13}$ is hydrogen, $C_{1-4}$alkyl, carbocyclyl or $R^{23}$; wherein $R^{13}$ is optionally substituted by one or more substituents selected from $R^{20}$ wherein $R^{20}$ is hydroxy, $C_{1-4}$alkylS(O)a wherein a is 0, $C_{1-4}$alkoxy, amino, carbocyclyl, heterocyclyl or mercapto; wherein $R^{20}$ may be independently optionally substituted on carbon by one or more $R^{22}$; $R^{22}$ is selected from hydroxy; and $R^{23}$ is carboxy.

In another further aspect of the invention, more preferably $R^{13}$ is hydrogen, methyl, ethyl, butyl or phenyl or $R^{23}$; wherein $R^{13}$ is optionally substituted by one or more substituents selected from $R^{20}$; wherein $R^{20}$ is hydroxy, methylthio, methoxy, amino, imidazolyl or mercapto; wherein $R^{20}$ may be independently optionally substituted on carbon by one or more $R^{22}$; $R^{22}$ is selected from hydroxy; and $R^{23}$ is carboxy.

In another further aspect of the invention, particularly $R^{13}$ is hydrogen, carboxy, hydroxymethyl, mercaptomethyl, methoxymethyl, methylthiomethyl, 2-methylthioethyl, 4-aminobutyl, 4-hydroxybenzyl, imidazol-5-ylmethyl or phenyl.

In another aspect more particularly $R^{13}$ is methylthiomethyl, methylsulphinylmethyl or methylsulphonylmethyl.

Preferably $R^{14}$ is hydrogen.

In another aspect of the invention, preferably $R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and $R^{20}$ is hydroxy.

In another aspect of the invention, more preferably $R^{14}$ is selected from hydrogen, methyl or phenyl; wherein said methyl or phenyl may be optionally substituted by one or more substituents selected from $R^{20}$; and $R^{20}$ is hydroxy.

In another aspect of the invention, particularly $R^{14}$ is hydrogen, phenyl or hydroxymethyl. Particularly $R^{15}$ is carboxy or sulpho.

In one aspect of the invention, more particularly $R^{15}$ is carboxy.

In another aspect of the invention, more particularly $R^{15}$ is sulpho.

Preferably $R^{15}$ is carboxy, sulpho, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-4}$alkyl.

More preferably $R^{15}$ is carboxy, sulpho, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl.

Preferably $R^{15}$ is carboxy, sulpho, —P(O)(OEt)(OEt), —P(O)(OH)(OEt), —P(O)(OH)(Me) or —P(O)(OEt)(Me).

Preferably $R^{15}$ is carboxy, sulpho, phosphono, —P(O)(OR$^e$)(OR$^f$), —P(O)(OH)(OR$^e$), —P(O)(OH) (R$^e$) or —P(O)(OR$^e$)(R$^f$) wherein R$^e$ and R$^f$ are independently selected from $C_{1-4}$alkyl or $R^{15}$ is a group of formula (IC) (as depicted above).

More preferably $R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl or $R^{15}$ is a group of formula (IC) (as depicted above).

Preferably $R^{15}$ is carboxy, sulpho, phosphono, —P(O)(OEt)(OEt), —P(O)(Ot-Bu)(Ot-Bu), —P(O)(OH)(OEt), —P(O)(OH)(Me) or —P(O)(OEt)(Me) or $R^{15}$ is a group of formula (IC) (as depicted above).

In one aspect of the invention, preferably $R^{15}$ is carboxy.

In another aspect of the invention, preferably $R^{15}$ is sulpho.

In another aspect of the invention, preferably $R^{15}$ is —P(O)(OH)(OEt).

In another aspect of the invention, preferably $R^{15}$ is —P(O)(OH)(Me).

In another aspect of the invention, preferably $R^{15}$ is —P(O)(OEt)(Me).

In one aspect of the invention, preferably $R^{24}$ is hydrogen.

In another aspect of the invention, preferably $R^{24}$ is $C_{1-4}$alkyl.

Preferably $R^{25}$ is hydrogen.

Preferably $R^{26}$ is carboxy.

Preferably p is 1 or 2; wherein the values of $R^{13}$ may be the same or different.

In one aspect of the invention, more preferably p is 1.

In another aspect of the invention, more preferably p is 2; wherein the values of $R^{13}$ may be the same or different.

In a further aspect of the invention, more preferably p is 3; wherein the values of $R^{13}$ may be the same or different.

In one aspect of the invention, preferably q is 0.

In a further aspect of the invention, preferably q is 1.

In one aspect of the invention, preferably r is 0.

In one aspect of the invention, more preferably r is 1.

In another aspect of the invention, more preferably r is 2; wherein the values of $R^{14}$ may be the same or different.

In a further aspect of the invention, more preferably r is 3; wherein the values of $R^{14}$ may be the same or different.

Preferably m is 0.

In another aspect of the invention, preferably m is 0 or 1.

Preferably n is 1.

In another aspect of the invention, preferably n is 1 or 2.

Preferably z is 1.

The group of formula (IA) wherein $R^7$ is hydrogen, methyl or phenyl, n is 1, Ring A is phenyl, thienyl or indolyl; wherein Ring A is optionally substituted by one or more substituents selected from halo, hydroxy or trifluoromethyl, m is 0 and $R^9$ is carboxy, —P(O)(OH)(OR$^c$) or a group of formula (IB).

The group of formula (IA) wherein: X is —O—.

Ring A is phenyl, thienyl or indolyl; wherein Ring A is optionally substituted by one or more substituents selected from halo, hydroxy, methoxy or trifluoromethyl;

$R^7$ is hydrogen, methyl or phenyl;
$R^8$ is hydrogen or methyl;
$R^9$ is hydrogen or methyl;
$R^{10}$ is hydrogen;
m is 0-2 wherein the values of $R^{10}$ may be the same or different; and $R^{11}$ is carboxy, —P(O)(OH)(OEt) or a group of formula (IB) (as depicted in claim 1); The group of formula (IB) wherein $R^{10}$ is hydrogen, hydroxymethyl or phenyl, p is 1 or 2; wherein the values of $R^{10}$ may be the same or different and $R^{11}$ is carboxy or sulpho.

The group of formula (IB) wherein:
$R^{12}$ is hydrogen or methyl;
$R^{13}$ is hydrogen, methyl, ethyl, butyl or phenyl or $R^{23}$; wherein $R^{13}$ is optionally substituted by one or more substituents selected from $R^{20}$; $R^{20}$ is hydroxy, methylthio, methoxy, amino, imidazolyl or mercapto; wherein $R^{20}$ may be independently optionally substituted on carbon by one or more hydroxy; $R^{23}$ is carboxy; Y is —NH— or —NHC(O)—; $R^{14}$ is selected from hydrogen, methyl or phenyl; wherein said methyl or phenyl may be optionally substituted by one or more substituents selected from hydroxy; $R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein $R^e$ and $R^f$ are independently selected from methyl or ethyl or $R^{15}$ is a group of formula (IC) (as depicted in claim 1);

p is 1-3 wherein the values of $R^{13}$ may be the same or different;

q is 0-1; and r is 0-3 wherein the values of $R^{14}$ may be the same or different;

The group of formula (IC) wherein
$R^{24}$ is hydrogen;
$R^{25}$ is hydrogen;
$R^{26}$ is carboxy; and
z is 1;

or a pharmaceutically acceptable salt, solvate, solvate of such a salt or a prodrug thereof.

Therefore in a further aspect of the invention, there is provided a compound of formula (I) as depicted above wherein:

$R^1$ and $R^2$ are independently selected from ethyl or butyl;
$R^3$ and $R^6$ are hydrogen;
$R^4$ is selected from halo, $C_{1-4}$alkoxy or $C_{1-4}$alkylS(O)$_a$ wherein a is 0 to 2; wherein that $R^4$ may be optionally substituted on carbon by one or more $R^{16}$; wherein $R^{16}$ is independently selected from hydroxy and N,N—($C_{1-4}$alkyl)$_2$amino;
$R^5$ is a group of formula (IA);
Ring A is aryl or heteroaryl; wherein Ring A is optionally substituted by one or more substituents selected from $R^{17}$; wherein
$R^{17}$ is selected from halo, hydroxy or $C_{1-4}$alkyl; wherein $R^{17}$ may be optionally substituted on carbon by one or more $R^{21}$; wherein
$R^{21}$ is selected from halo;
$R^7$ is hydrogen, $C_{1-4}$alkyl or carbocyclyl;
$R^{11}$ is carboxy, —P(O)(OH)(OR$^c$) or a group of formula (IB) (as depicted above);
$R^{13}$ is hydrogen, $C_{1-4}$alkyl or carbocyclyl; wherein $R^{13}$ is optionally substituted by one or more substituents selected from $R^{20}$; wherein
$R^{20}$ is hydroxy;
$R^{15}$ is carboxy or sulpho;
p is 1 or 2; wherein the values of $R^{13}$ may be the same or different;
m is 0; and
n is 1;

or a pharmaceutically acceptable salt, solvate, solvate of such a salt or a prodrug thereof.

Therefore in an additional aspect of the invention, there is provided a compound of formula (I) as depicted above wherein:

$R^1$ and $R^2$ are both butyl or one of $R^1$ and $R^2$ is ethyl and the other is butyl;
$R^4$ is methylthio;
$R^5$ is a group of formula (IA) (as depicted above);
$R^3$ and $R^6$ are hydrogen;
Ring A is phenyl;
$R^7$ is hydrogen;
$R^{11}$ is a group of formula (IB) (as depicted above);
$R^{13}$ is hydrogen or hydroxymethyl;
$R^{15}$ is carboxy or sulpho;
p is 1 or 2; wherein the values of $R^{13}$ may be the same or different;
m is 0;
n is 1;

or a pharmaceutically acceptable salt, solvate, solvate of such a salt or a prodrug thereof.

Therefore in an additional further aspect of the invention, there is provided a compound of formula (I) as depicted above wherein:
$R^1$ and $R^2$ are independently selected from ethyl or butyl;
$R^3$ and $R^6$ are hydrogen;
$R^4$ is selected from halo, $C_{1-4}$alkoxy or $C_{1-4}$alkylS(O)$_a$ wherein a is 0 to 2; wherein that $R^4$ may be optionally substituted on carbon by one or more $R^{16}$; wherein $R^{16}$ is independently selected from hydroxy and N,N—($C_{1-4}$alkyl)$_2$amino;
$R^5$ is a group of formula (IA);
Ring A is aryl or heteroaryl; wherein Ring A is optionally substituted by one or more substituents selected from $R^{17}$;
$R^7$ is hydrogen, $C_{1-4}$alkyl or carbocyclyl;
$R^8$ is hydrogen or methyl;
$R^9$ is hydrogen or methyl;
$R^{11}$ is carboxy, —P(O)(OH)(OR$^c$) or a group of formula (IB) (as depicted above);
X is —NH— or —NHC(O)—;
$R^{12}$ is hydrogen or methyl;
$R^{13}$ is hydrogen, $C_{1-4}$alkyl or carbocyclyl; wherein $R^{13}$ is optionally substituted by one or more substituents selected from $R^{20}$;
$R^{14}$ is hydrogen;
$R^{15}$ is carboxy or sulpho;
$R^{17}$ is selected from halo, hydroxy, $C_{1-4}$alkyl or $C_{1-4}$alkoxy; wherein $R^{17}$ may be optionally substituted on carbon by one or more $R^{21}$;
$R^{20}$ is hydroxy, carboxy, carbocyclyl or amino; wherein $R^{20}$ may be optionally substituted on carbon by one or more $R^{22}$;
$R^{21}$ is selected from halo;
$R^{22}$ is hydroxy;
p is 1-3; wherein the values of $R^{13}$ may be the same or different.
q is 0-1;
r is 0-3; wherein the values of $R^{14}$ may be the same or different; and wherein if q is 1, r is not 0;
m is 0-2; and
n is 1-3;
or a pharmaceutically acceptable salt, solvate, solvate of such a salt or a prodrug thereof.

Therefore in another additional further aspect of the invention, there is provided a compound of formula (I) as depicted above wherein:
$R^1$ and $R^2$ are independently selected from $C_{1-4}$alkyl;
$R^x$ and $R^y$ are both hydrogen;
$R^z$ is selected from halo, amino, $C_{1-6}$alkyl, $C_{1-6}$alkoxycarbonylamino or N'—($C_{1-6}$alkyl)ureido;
v is 0 or 1;
$R^3$ and $R^6$ are hydrogen;
one of $R^4$ and $R^5$ is a group of formula (IA) (as depicted above) and the other is selected from hydrogen, halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy, carboxy and N,N—($C_{1-4}$alkyl)2amino;
X is —O—;
$R^7$ is hydrogen, methyl or phenyl;
$R^8$ is hydrogen or methyl;
Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo;
$R^9$ is hydrogen or methyl;
$R^{10}$ is hydrogen;
$R^{11}$ is carboxy, —P(O)(OH)(OR$^c$) wherein R$^c$ is selected from $C_{1-4}$alkyl or a group of formula (IB) (as depicted above);
$R^{12}$ is hydrogen or methyl;
Y is —NH— or —NHC(O)—;
$R^{13}$ is hydrogen, $C_{1-4}$alkyl, carbocyclyl or $R^{23}$; wherein $R^{13}$ is optionally substituted by one or more substituents selected from $R^{20}$; wherein $R^{20}$ is hydroxy, $C_{1-4}$alkylS(O)$_a$ wherein a is 0, $C_{1-4}$alkoxy, amino, carbocyclyl, heterocyclyl or mercapto; wherein $R^{20}$ may be independently optionally substituted on carbon by one or more $R^{22}$; $R^{22}$ is selected from hydroxy; and $R^{23}$ is carboxy;
$R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and $R^{20}$ is hydroxy;
$R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-4}$alkyl or $R^{15}$ is a group of formula (IC) (as depicted above);
$R^{24}$ is hydrogen;
$R^{25}$ is hydrogen;
$R^{26}$ is carboxy;
p is 1-3; wherein the values of $R^{13}$ may be the same or different;
q is 0-1;
r is 0-3; wherein the values of $R^{14}$ may be the same or different;
m is 0-2; wherein the values of $R^{10}$ may be the same or different;
n is 1-2; wherein the values of $R^7$ may be the same or different;
z is 0-1; wherein the values of $R^{25}$ may be the same or different;
or a pharmaceutically acceptable salt, solvate, solvate of such a salt or a prodrug thereof. In another aspect of the invention, preferred compounds of the invention are any one of the Examples or a pharmaceutically acceptable salt, solvate, solvate of such a salt or a prodrug thereof.

In another aspect of the invention, preferred compounds of the invention are any one of the Examples or a pharmaceutically acceptable salt, solvate, solvate of such a salt or a prodrug thereof.

An aspect of the invention is a compound of formula II

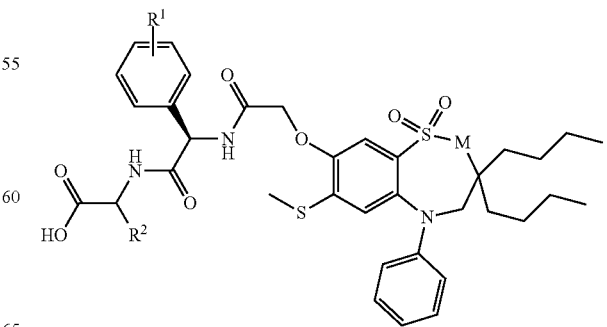

Formula II wherein

M is CH$_2$ or NH;

R$^1$ is H or hydroxy;

R$^2$ is H, CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —CH(CH$_3$)CH$_2$CH$_3$, —CH$_2$OH, —CH$_2$OCH$_3$, —CH(OH)CH$_3$, —CH$_2$SCH$_3$, or —CH$_2$CH$_2$SCH$_3$;

for use in the prophylaxis or treatment of a liver disease.

Examples of useful substances in accordance with the invention are:

1,1-Dioxo-3,3-dibutyl-5-phenyl-7-methylthio-8-(N—{(R)-α-[N-(carboxymethyl)carbamoyl]benzyl} carbamoyl-methoxy)-2,3,4,5-tetrahydro-1,2,5-benzothiadiazepine, 1,1-Dioxo-3,3-dibutyl-5-phenyl-7-methylthio-8-(N—{(R)-α-[N'—((S)-1-carboxyethyl) carbamoyl]benzyl} carbamoylmethoxy)-2,3,4,5-tetrahydro-1,5-benzothiazepine, 1,1-Dioxo-3,3-dibutyl-5-phenyl-7-methylthio-8-(N—{(R)-α-[N—((S)-1-carboxypropyl) carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((R)-1-carboxy-2-methylthioethyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxybutyl) carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxyethyl) carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N'—((S)-1-carboxypropyl) carbamoyl]-4-hydroxybenzyl} carbamoylmethoxy)-2,3,4,5-tetrahydro-1, 5-benzothiazepine, 1,1-Dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine and 1,1-dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine.

Compounds of formula (I) or formula (II) may have chiral centres and/or geometric isomeric centres (E- and Z-isomers), and it is to be understood that the invention encompasses all such optical, diastereoisomers and geometric isomers that possess IBAT inhibitory activity. The invention relates to any and all tautomeric forms of the compounds of the formula (I) or formula (II) that possess IBAT inhibitory activity.

The invention also relates all possible isomers of the compounds of the invention such as, optical and/or geometrical, pure or as a mixture, in all proportions, of the said compounds of formulas I and II and those specifically mentioned and the possible tautomeric forms In certain embodiments, compounds described herein have one or more chiral centres. As such, all stereoisomers are envisioned herein. In various embodiments, compounds described herein are present in optically active or racemic forms. It is to be understood that the compounds of the present invention encompasses racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer are utilized as the therapeutic compound described herein. In certain embodiments, compounds described herein, contains one or more chiral centres. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

The compounds may exist in free-acid or free-base form, or in a pharmaceutically acceptable salt form. In certain embodiments, a compound described herein exists in an unsolvated or solvated form, wherein solvated forms comprise any pharmaceutically acceptable solvent, e.g., water, ethanol, and the like.

The invention further regards a composition comprising at least one IBAT inhibitor of Formula (I) or Formula (II), for use in the prophylaxis and/or treatment of a liver disease.

An aspect of the invention is the use of a compound of Formula (I) or Formula (II), for the preparation of a medicine for the treatment of a liver disease.

An IBAT inhibitor of Formula I or Formula II) may be used together with at least one other therapeutically active compound as described herein, in the preparation of a medicament for the prophylactic and/or therapeutic treatment of a liver disease.

Liver Diseases

Liver disease is herein defined as any Bile Acid (BA) dependent disease in the liver and in organs connected therewith, such as the pancreas portal vein, the liver parenchyma, the intrahepatic biliary tree, the extrahepatic biliary tree, and the gall bladder.

Ileal bile acid transporter (IBAT) is the main mechanism for re-absorption of bile acids from the GI tract. Partial or full blockade of that mechanism will result in lower concentration of bile acids in the small bowel wall, the portal vein, the liver parenchyma, the intrahepatic biliary tree, the extrahepatic biliary tree, and in the gall bladder. Diseases which may benefit from partial or full blockade of the IBAT mechanism may be those having a primary pathophysiological defect, causing or having symptoms of too high concentration of bile acids in serum and in the above organs.

An aspect of the invention is a compound of Formula (I) or Formula (II) as defined above, for use in the prophylaxis or treatment of liver parenchyma; an Inherited metabolic disorder of the liver; Byler syndrome; a primary defect of bile acid (BA) synthesis such as cerebrotendinous, or xanthomatosis; a secondary defect such as Zellweger's syndrome, neonatal hepatitis, cystic fibrosis, manifestations in the liver, ALGS (Alagilles syndrome), PFIC (progressive familial intrahepatic cholestasis, autoimmune hepatitis, primary biliary cirrhosis (PBC), liver fibrosis, non alcoholic fatty liver disease, NAFLD/NASH, portal hypertension, general cholestasis such as in jaundice due to drugs or during pregnancy, intra and extrahepatic cholestasis such as hereditary forms of cholestasis such as PFIC1, Primary sclerosing cholangitis, gall stones and choledocholithiasis, malignancy causing obstruction of the biliary tree, symptoms (scratching, pruritus) due to cholestasis/jaundice, pancreatitis, chronic autoimmune liver disease leading to progressive cholestasis, or pruritus of cholestatic liver disease.

An aspect of the invention is a compound of Formula (I) or Formula (II) as defined above, for use in the prophylaxis or treatment of a hepatic disorder or a hepatic related condition, fatty liver, hepatic steatosis, non-alcoholic steatohepatitis (NASH), alcoholic hepatitis, acute fatty liver, fatty liver of pregnancy, drug-induced hepatitis, iron overload disorders, hepatic fibrosis, hepatic cirrhosis, hepatoma, viral hepatitis and problems in relation to tumours and neoplasmas of the liver, of the biliary tract and of the pancreas.

Combination with Other Active Substances

An aspect of the invention is an IBAT inhibitor according to formula (I) or Formula (II) as defined above, in combination with at least one other therapeutically active substance. The at least one other therapeutically active substance may be an IBAT inhibitor compound.

Incretines and Hormones Produced by the L Cells

The at least one other therapeutically active substance may be an Incretine or a hormone produced by the L cells.

In an aspect of the invention, the at least one other therapeutically active substance is a L-cell endocrine peptide enhancer such as a GLP-1 enhancer. Examples of a GLP-1 enhancer useful in accordance with the invention are GLP-1, a GLP-1 secretion enhancer, a GLP-1 degradation inhibitor, or a combination thereof.

In an aspect of the invention, the L-cell endocrine peptide enhancer is a GLP-2 enhancer such as GLP-2, a GLP-2 secretion enhancer, a GLP-2 degradation inhibitor, or a combination thereof.

In an aspect of the invention the L-cell endocrine peptide enhancer is a PYY enhancer such as an oxyntomodulin enhancer.

Incretin Mimetics

In an aspect of the invention, the at least one other therapeutically active substance is an incretin mimetic such as exenatide (Byetta®).

One aspect of the invention is an oral combination of an IBAT inhibitor of Formula (I) or Formula (II) as disclosed herein and a DPP-IV inhibitor.

Enteroendocrine Peptides

In an aspect of the invention, the at least one other therapeutically active substance is an enteroendocrine peptide such as GLP-1 or GLP-1 analogs, for example Taspoglutide® (Ipsen), or the like.

Combination Therapy with an IBAT Inhibitor and a DPP-IV Inhibitor

In an aspect of the invention, the at least one other therapeutically active substance is a DPP-IV inhibitor.

One aspect of the invention is a combination of an IBAT-inhibitor and metformin and/or sitagliptin (Janumet®) and/or DPP-IV inhibitors suitable for use with the methods described herein include but are not limited to (2S)-1-{2-[(3-hydroxy-1-adamantyl)amino]-acetyl}pyrrolidine-2-carbonitrile (vildagliptin), (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[-3.1.0]hexane-3-carbonitrile (saxagliptin), and 2-({6-[(3R)-3-aminopiperidin-1-yl]-3-methyl-2,4-dioxo-3,4-dihydropyrimidi-n-1(2H)-yl}methyl)benzonitrile (alogliptin).

TGR5 Receptor Modulators

In one aspect of the invention, the at least one other therapeutically active substance is a TGR5 agonist. TGR5 modulators (e.g. agonists) include, but are not limited to, the compounds described in WO 2008/091540, WO 2008/067219 and U.S. Appl. No. 2008/0221161.

Thiazolidinediones

In one embodiment of the invention, the at least one other therapeutically active substance is a thiazolidinedione such as Rosiglitazone (Avandia), Pioglitazone (Actos), Troglitazone (Rezulin), MCC-555, rivoglitazone, ciglitazone or the like.

Combination Therapy with an IBAT INHIBITOR, a Biliary Shunt and a DPP-IV Inhibitor In one embodiment of the invention, an IBAT INHIBITOR of Formula (I) or Formula (II) as described herein, is administered in combination with a DPP-IV inhibitor and/or a biliary shunt. Examples of biliary shunts include but are not limited to shunts described in WO 2007/0050628, which disclosure is incorporated herein by reference.

As used herein, the term "additive effect" describes the combined effect of two (or more) pharmaceutically active agents that is equal to the sum of the effect of each agent given alone. A synergistic effect is one in which the combined effect of two (or more) pharmaceutically active agents is greater than the sum of the effect of each agent given alone. Any suitable combination of an ASBTI with one or more of the aforementioned other active ingredients and optionally with one or more other pharmacologically active substances is contemplated as being within the scope of the methods described herein.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

The invention also regards IBAT inhibitor compounds described herein in combination with at least one bile acid binder e.g. a resin such as cholestyramine, cholestipol and colesevelam.

Bile Acid Binders (Bile Acid Sequestrants, Resins)

In one embodiment of the invention, an IBAT inhibitor of formula (I) or Formula (II) as defined above, may be administered as a pharmaceutical formulation also comprising at least one bile acid binder, said formulation being designed to deliver the bile acid binder in the colon and the IBAT inhibitor in the small intestine.

Examples of useful bile acid binders according to the invention are Cholestyramine, which is a hydrophilic polyacrylic quaternary ammonium anion exchange resin, known to be effective in reducing blood cholesterol levels. Cholestyramine, and various compositions including cholestyramine, are described, for example, in British Pat Nos. 929,391 and 1,286, 949; and U.S. Pat. Nos. 3,383,281; 3,308,020; 3,769,399; 3,846,541; 3,974,272; 4,172,120; 4,252,790; 4,340,585; 4,814,354; 4,874,744; 4,895,723; 5,695,749; and 6,066,336. Cholestyramine is commercially available from Novopharm, USA Inc (Questrans Light), Upsher-Smith (PREVALITE (D), and Apothecon. As used herein, "cholestyramine" includes any such composition comprising cholestyramine, or pharmaceutically acceptable salts thereof. These are also called Questrans™

Questran Light Questrans Light (cholestyramine) is a non-absorbable anion binding resin FDA approved for the treatment of hypercholesterolemia.

An amine polymer having a first substituent, bound to a first amine of the amine polymer, that includes a hydrophobic aliphatic moiety, and a second substituent, bound to a second amine of the amine polymer, that includes an aliphatic quaternary amine-containing moiety as described in U.S. Pat. Nos. 5,693,675 and 5,607,669.

The salt of an alkylated and cross linked polymer comprising the reaction product of: (a) one or more cross linked polymers, or salts and copolymers thereof having a repeat unit selected from the group consisting of: $(NR-CH_2CH_2)n$ (2) and $(NR-CH_2CH_2-NR-CH_2CH_2-NR-CH_2CHOH-CH_2)n$ (3) where n is a positive integer and each R, independently, is H or a C1-C8 alkyl group; (b) at least one aliphatic alkylating agent, said reaction product characterized in that: (i) at least some of the nitrogen atoms in said repeat units unreacted with said alkylating agent; (ii) less than 10 mol percent of the nitrogen atoms in said repeat units reacting with said alkylating agent forming quaternary ammonium units; and (iii) a fixed positive charge and one or more counter ions, such as Colesevelam and colesevelam hydrochloride.

Useful bile acid binders in accordance with the invention are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Another useful bile acid binder is a water insoluble non-toxic polymeric amine having a molecular weight in excess of 3,000, having the property of binding at least 30% of the available glycocholic acid within 5 minutes when exposed to an aqueous solution of an equal weight of said acid, having a polymer skeleton inert to digestive enzymes, and having a water content greater than 65% after equilibration with air at 100% relative humidity, e.g., cholestipol described in U.S. Pat. No. 3,383,281, In a further aspect of the invention a suitable bile acid binder is one of cholestyramine, cholestipol or colesevelam.

A preferred aspect of the present invention is the use of colesevelam as the bile acid binder.

The compositions of the invention may further comprise statins e.g an HMG Co-A reductase inhibitor, or a pharmaceutically acceptable salt, solvate, solvate of such a salt or a prodrug thereof, in association with a pharmaceutically acceptable diluent or carrier.

One embodiment of the invention relates to a combined oral pharmaceutical formulation comprising an IBAT inhibitor compound of formula (I) or Formula (II) as defined above or a pharmaceutically acceptable salt, solvate, solvate of such a salt or a prodrug thereof and a bile acid binder or a pharmaceutically acceptable salt, solvate, solvate of such a salt or a prodrug thereof, said formulation being designed to deliver the bile acid binder in the colon and the IBAT inhibitor in the small intestine.

One embodiment of the present invention is a pharmaceutical formulation comprising a core of a bile acid binder formulated for release in the colon, surrounded by an outer layer comprising an IBAT inhibitor of formula (I) or Formula (II) as defined above, and formulated for immediate release or for delayed release in the distal jejunum or the proximal ileum.

Statins

In another aspect of the invention, an IBAT inhibitor compound e.g. a compound of formula (I) or formula (II) as defined above or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art.

Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl (methylsulphonyl) amino] pyrimidin-5-yl] (3R, 5S)-3,5-dihydroxyhept-6-enoic acid (rosuvastatin), or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4-(4-fluorophenyl)-6-isopropyl-2-[methyl (methylsulphonyl) amino] pyrimidin-5-yl] (3R,5S)-3,5-dihydroxyhept-6-enoic acid (rosuvastatin), or a pharmaceutically acceptable salt, solvate, solvate of such a salt or a prodrug thereof. Other particular statin are rosuvastatin calcium salt and pitavastatin (HMG Co A reductase).

In an additional aspect of the invention, the compound of formula (I) or formula (II) as defined above, or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising a compound of formula (I) or formula (II) as defined above, or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with a compound of formula (I) or formula (II) as defined above, or a pharmaceutically acceptable salt, solvate, solvate of such a salt or a prodrug thereof on lipid lowering.

The composition may further comprise a PPAR alpha and/or gamma agonist, or a pharmaceutically acceptable salt thereof.

A CETP (cholesteryl ester transfer protein) inhibitor, for example those referenced and described in WO 00/38725 page 7 line 22-page 10, line 17 which are incorporated herein by reference.

A cholesterol absorption antagonist for example azetidinones such as SCH 58235 and those described in U.S. Pat. No. 5,767,115 which are incorporated herein by reference; MTP (microsomal transfer protein) inhibitor for example those described in Science, 282, 751-54, 1998 which are incorporated herein by reference;

A fibric acid derivative; for example clofibrate, gemfibrozil, fenofibrate, ciprofibrate and bezafibrate;

A nicotinic acid derivative, for example, nicotinic acid (niacin), acipimox and niceritrol;

A phytosterol compound for example stanols;

Probucol;

An anti-obesity compound for example orlistat (EP 129,748) and sibutramine (GB 2,184,122 and U.S. Pat. No. 4,929,629);

An antihypertensive compound for example an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, a diuretic or a vasodilator;

Insulin;

Sulphonylureas including glibenclamide and/or tolbutamide.

Biguanides

In some embodiments, the additional therapeutic agent is a biguanide. In some instances, biguanides reduce blood and/or plasma glucose levels. Examples of biguanides include and are not limited to metformin, buformin, phenformin, proguanil or the like.

Acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Angiotensin II Antagonists

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

PPAR alpha and/or gamma and/or delta agonists or a pharmaceutical acceptable salt thereof.

In another aspect of the invention, the IBAT inhibitor compound, or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39,665, Expert Opinion on Therapeutic Patents, 10 (5), 623-634 (in particular the compounds described in the patent applications listed on page 634) and J Med Chem, 2000, 43,527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433.

Particularly a PPAR alpha and/or gamma agonist refers to (S)-2-ethoxy-3-[4-(2-{4-methanesulphonyloxyphenyl} ethoxy) phenyl] propanoic acid and pharmaceutically acceptable salts thereof.

According to one embodiment the substances of the invention are used together with one or more antidiabetics hypoglycaemic active ingredients, cholesterol absorption inhibitors, PPAR delta agonists, fibrates, MTP inhibitors, bile acid absorption inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, alpha-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose-1,6-bisphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, modulators of GPR40, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, beta 3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-beta agonists or amphetamines.

One aspect of the invention is a method for the treatment of a liver disease, whereby an IBAT inhibitor of Formula (I) or Formula (II) as defined above is brought into contact with the distal ileum of an individual in need of such treatment.

In one embodiment of the invention, an IBAT inhibitor of Formula (I) or Formula (II) as defined above, is administered in combination with a second therapeutic agent selected from a DPP-IV inhibitor, a thiazolidinedione, or an analogue thereof, or a TGR5 agonist.

In certain embodiments, IBAT inhibitor compounds described herein are combined with or utilized in combination with one or more of the following therapeutic agents in any combination: insulin, insulin-mimetics, DPP-IV inhibitors, or TGR5 modulators.

Further active substances to be combined with one or more IBAT inhibitors of the invention may be chosen from one or more of the following substances:
Ursodeoxycholic acid; nor-ursodeoxycholic acid; Rifampicin and related rifamycin derivatives as described in U.S. Pat. No. 3,342,810; opiat antagonists such as Naloxone and Naltrexone; serotonin antagonists such as 5-HT3 receptor antagonists and 5 HT2 antagonists, e.g. Trazodone, Nefazodone, Amoxapine, Clozapine; antihistamines such as Brompheniramine, Chlorpheniramine Dimenhydrinate, Diphenhydramine, Doxylamine Loratadine Cetirizine; serotonin reuptake inhibitors such as Citalopram, Dapoxetine, Escitalopram, Fluoxetine, Fluvoxamine, lindalpine, Pparoxetine, Sertraline, Zimelidine; corticosteroids such as glucocorticoids and mineralocorticoids e.g. chosen from Hydrocortisone (Cortisol), Cortisone and acetate, Prednisone, Prednisolone, Methylprednisolone, Dexamethasone, Betamethasone, Triamcinolone, Beclometasone, Fludrocortisone and acetate, Deoxycorticosterone and acetate (DOCA) Aldosterone.

Examples of PPAR delta agonists are GW-501516 (501516, GSK-516, GW-516, GW-1516; a peroxisome proliferator-activated receptor (PPAR)-delta agonist, and several other compounds developed from GW-501516, including GI-262570, GW-0072, GW-7845 and GW-7647.

According to one embodiment the IBAT inhibitor may be combined with one or more of Atreleuton, Eprotirome, Losmapimod, Ezetimibe (SCH58235) Bezafibrate, Fenofibrate, Varespladib, Darapladib, Lomitapide, Implitapide, Rosiglitazone, Dalcetrapib, Anacetrapib, Lorcaserin, Dapagliflozin, Canagliflozin, Sergliflozin ASP-1941 Orlistat, Pioglitazone, Sodelglitazar, Netoglitazone, Indeglitazar, Naveglitazar, Lobeglitazone, Aleglitazar, Bromocriptine, Tesofensine, Monoamine, Alogliptin, Vildagliptin, Saxagliptin, Sitagliptin, Denagliptin, Gemigliptin, Linagliptin, Dutogliptin, Teneligliptin, LC-150444, Laropiprant extended release niacin, Simvastatin ezetimibe, Rosuvastatin fenofibrate, Rosuvastatin ezetimibe and Atorvastatin ezetimibe.

Combinations with Tredaptive, Vytorin and Certriad may be used.

According to one embodiment the IBAT inhibitor may be combined with one or more of any of the above mentioned other compounds.

According to one embodiment the IBAT inhibitors of the present invention are combined with at least one other active substance selected from dipeptidyl peptidase-IV-inhibitors, PPAR γ agonists, statins and bile acid binders in any combination.

According to one embodiment the IBAT inhibitors of the present invention are combined with at least one DPPIV, at least one PPAR γ agonist, such as Sitagliptin and Pioglitazon.

According to one other embodiment the IBAT inhibitors of the present invention are combined with at least one DPPIV and at least one statin e.g. Sitagliptin and Simvastatin.

Another active substance which may be combined with the IBAT inhibitors of the invention is ursodeoxycholic acid.

According to one embodiment the invention relates to a composition comprising one or more BAT inhibitors of the invention and cholestyramin and/or colesevelam and/or cholestipol.

According to one embodiment the invention relates to a composition comprising one or more of the compounds of Example 1, 2, 3, 4, 5, 6, 7, 8, 9, 10, 11, 12, 13 and 14 and cholestyramin and/or colesevelam and/or cholestipol.

According another embodiment the invention relates to a composition comprising one or more of the compounds of 1,1-Dioxo-3,3-dibutyl-5-phenyl-7-methylthio-8-(N—{(R)-1'-phenyl-1'-[N'-(carboxymethyl)-carbamoyl] methyl}carbamoylmethoxy)-2,3,4,5-tetrahydro-1,5-benzothiazepine (Example 5) and cholestyramin and/or colesevelam and/or cholestipol.

According another embodiment the invention relates to a composition comprising one or more of the compounds of 1,1-Dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine (Example 13), and cholestyramin and/or colesevelam and/or cholestipol.

According another embodiment the invention relates to a composition comprising one or more of the compounds of 1,1-Dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine (Example 14) and cholestyramin and/or colesevelam and/or cholestipol.

Carriers and Excipients

The compositions of the invention may further comprise a pharmaceutically acceptable diluent or carrier.

Pharmaceutical compositions may be formulated as known in the art using one or more physiologically acceptable carriers including, e.g., excipients and depending on the route of administration chosen.

A carrier includes, in some embodiments, a pharmaceutically acceptable excipient and is selected on the basis of compatibility with compounds described herein, such as, compounds of any of Formula I and II, and the release profile properties of the desired dosage form.

Exemplary carrier materials include, e.g., binders, suspending agents, disintegration agents, filling agents, surfactants, solubilizers, stabilizers, lubricants, wetting agents, diluents.

Pharmaceutical compositions and carriers are described, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A mixture of a compound of Formula I and II and possibly also other active compounds mentioned herein, with other chemical components, such as carriers, stabilizers, diluents, dispersing agents, suspending agents, thickening agents, and/or excipients may be formulated into a composition. In certain embodiments, therapeutically effective amounts of compounds described herein are administered in a pharmaceutical composition to an individual having a disease, disorder, or condition to be treated. In specific embodiments, the individual is a human. The compounds described herein are either utilized separately or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

The pharmaceutical compositions described herein are formulated as a dosage form. As such, in some embodiments, provided herein does a dosage form comprise a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include an additional therapeutic compound described herein and one or more pharmaceutically acceptable additives such as a compatible carrier, binder, filling agent, suspending agent, flavouring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in Remington's Pharmaceutical Sciences, 20th Edition (2000), a film coating is provided around the formulation of the compound of Formula I-II. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

Method of Treatment

The invention also regards a method for treatment and/or prophylaxis of a liver disease, in a warm-blooded animal, such as man, in need of such treatment and/or prophylaxis comprising administering an effective amount of a compound or a composition according to the invention to the individual.

A method for treating any of the diseases or conditions described herein in an individual in need of such treatment, may involve administration of pharmaceutical compositions containing at least one IBAT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

Dosage Forms

The pharmaceutical solid dosage forms may optionally include additional therapeutic compounds and one or more pharmaceutically acceptable additives such as a compatible carrier, binder, filling agent, suspending agent, flavouring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in Remington's Pharmaceutical Sciences, 20th Edition (2000), a film coating is provided around the formulation of the compound of Formula I-II. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

An IBAT inhibitor of Formula I and II may be used in the preparation of medicaments for the prophylactic and/or therapeutic treatment of obesity and/or diabetes. A method for treating any of the diseases or conditions described herein in an individual in need of such treatment, involves administration of pharmaceutical compositions containing at least one IBAT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

A dosage form comprises a matrix that allows for controlled release of an active agent in the distal jejunum, proximal ileum, distal ileum and/or the colon. In some embodiments, a dosage form comprises a polymer that is pH sensitive (e.g., a MMX™ matrix from Cosmo Pharmaceuticals) and allows for controlled release of an active agent in the ileum and/or the colon. Examples of such pH sensitive polymers suitable for controlled release include and are not limited to polyacrylic polymers (e.g., anionic polymers of methacrylic acid and/or methacrylic acid esters, e.g., Carbopol® polymers, (CAS number 9063-87-0) that comprise acidic groups (e.g., —COOH, —SO$_3$H) and swell in basic pH of the intestine (e.g., pH of about 7 to about 8). In some embodiments, a dosage form suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an IBAT to the distal ileum. In some embodiments, a dosage form comprising an IBAT is coated with an enteric polymer (e.g., Eudragit® S-100, cas number 25086-15-1), cellulose acetate phthalate, polyvinylacetate phthalate, hydroxypropylmethylcellulose phthalate, anionic polymers of methacrylic acid, methacrylic acid esters or the like) for site specific delivery to the ileum and/or the colon. In some embodiments, bacterially activated systems are suitable for targeted delivery to the ileum. Examples of micro-flora activated systems include dosage forms comprising pectin, galactomannan, and/or Azo hydrogels and/or glycoside conjugates (e.g., conjugates of D-galactoside, beta-D-xylopyranoside or the like) of the active agent. Examples of gastrointestinal micro-flora enzymes include bacterial glycosidases such as, for example, D-galactosidase, beta-D-glucosidase, alpha-L-arabinofuranosidase, beta-D-xylopyranosidase or the like.

Coated units may be filled into hard gelatine capsules or mixed with tablet excipients, such as fillers, binders, disintegrants, lubricants and other pharmaceutically acceptable additives, and be compressed into tablets. The compressed tablet is optionally covered with film-forming agents to obtain a smooth surface of the tablet and further enhance the mechanical stability of the tablet during packaging and transport. Such a tablet coat, which may be applied on a multiple unit tablet or a conventional tablet, may further comprise additives like anti-tacking agents, colorants and pigments or other additives to improve the tablet appearance.

Suitable drugs for the new formulations are IBAT inhibitor compounds such as described in the above-discussed documents, hereby incorporated by references.

The IBAT inhibitor compound could alternatively be a low permeability drug as defined in the Biopharmaceutical Classification System proposed by FDA.

A combination therapy according to the invention should preferably comprise simultaneously, separately or sequentially administration of an IBAT inhibitor compound and a bile acid binder. The IBAT inhibitor could preferably be formulated for ileum delivery and the bile acid binder could preferably be formulation for colon release.

Dosage

The compound of formula (I), or a pharmaceutically acceptable salt, solvate, solvate of such a salt or a prodrug thereof, will normally be administered to a warm-blooded animal at a unit dose within the range 5-5000 mg per square meter body area of the animal, i.e. approximately 0.1-100 mg or 0.01-50 mg, and this normally provides a therapeutically-effective dose. A unit dose form such as a tablet or capsule will usually contain, for example 1-250 mg of active ingredient. Preferably a daily dose in the range of 1-50 mg is employed. In another aspect a daily dose in the rage of 0.02-20 mg is employed. However the daily dose will necessarily be varied depending upon the host treated, the particular route of administration, and the severity of the illness being treated.

Accordingly the optimum dosage may be determined by the practitioner who is treating any particular patient.

The size of the dose required for the therapeutic or prophylactic treatment will necessarily be varied depending on the host treated, the route of administration and the severity of the illness being treated. A unit dose in the range, for example, 1-100, preferably 1-50 is envisaged. The daily dose can be administered as a single dose or divided into one, two, three or more unit doses.

A pharmaceutical formulation according to the present invention with a targeted delivery in the gastro intestinal tract provides a reduced systemic exposure, as can be measured by the area under the drug plasma concentration versus time curve (AUC) or 7α-hydroxy-4-cholesten-3-one (C4), while maintaining or even increasing the therapeutic effect, as e.g. measured by serum cholesterol reduction.

A combination therapy comprising an IBAT inhibitor and a bile acid binder comprises preferably a low daily dose of the bile acid binder, such as less than 5 g of a resin, and more preferably less than 2 g. A dosage form with colon release of the bile acid binder could be constructed by any of the above described principles for delayed release formulations.

A combination therapy comprising an IBAT inhibitor and a bile acid binder may comprise a low daily dose of the bile acid binder, such as less than 5 g of a resin, and more preferably less than 4, 3, 2 or less than 1 g. Suitable ranges may be 0.1-5 g, 0.5-4 g, 1-3 g, 2-4 g, 2-3 g per day. A dosage form with colon release of the bile acid binder could be constructed by any of the above described principles for delayed release formulations.

A tablet may consist of an inner core of 1-1000 mg, e.g. 200-800 mg, 10-400 mg, 10-200 mg or 20-80 mg acid binder in a colonic delivery formulation and an outer lamina with 1-100 mg, 5-50 mg e.g. 1-20 mg of an IBAT inhibitor.

The daily dose of IBAT inhibitor and/or bile acid binder can be administered as a single dose or divided into one, two, three or more unit doses.

Dosing three times a day with 400 mg of colesevelam in a colonic release formulation will give an adequate binding of bile acids in the colon as the total luminal volume is expected to be about 100 ml, which is in accordance to an accepted pharmacokinetic calculation volume of 250 to 300 ml for the small gut. The daily recommended total dose of colesevelam to block bile acid absorption in total gut of humans is 3750 mg/day.

Kit

Further, the invention relates to a kit comprising compound or a composition according to the invention and possibly also an instruction for use.

According to a further aspect of the present invention there is provided a kit comprising an BAT inhibitor according to the invention or a pharmaceutically acceptable salt, solvate, solvate of such a salt or a prodrug thereof, and an instruction for use.

According to a further aspect of the present invention there is provided a kit comprising an BAT inhibitor according to the invention or a pharmaceutically acceptable salt, solvate, solvate of such a salt or a prodrug thereof, and any of the above mentioned substances for use in combination, or a pharmaceutically acceptable salt, solvate, solvate of such a salt or a prodrug thereof.

According to a further aspect of the present invention there is provided a kit comprising: a) an IBAT inhibitor according to the invention or a pharmaceutically acceptable salt, solvate, solvate of such a salt or a prodrug thereof, in a first unit dosage form; b) any of the above mentioned substances for use in combination or a pharmaceutically acceptable salt, solvate, solvate of such a salt or a prodrug thereof; in a second unit dosage form; and c) container means for containing said first and second dosage forms.

The following contemplated Examples are intended to illustrate, but in no way limit the scope of the invention. All references cited herein are hereby incorporated by reference in their entirety.

The expression "comprising" as used herein should be understood to include, but not be limited to, the stated items.

Example 1

1,1-Dioxo-3,3-dibutyl-5-phenyl-7-methylthio-8-(N—{(R)-α-[N-(carboxymethyl)carbamoyl]benzyl} carbamoylmethoxy)-2,3,4,5-tetrahydro-1,2,5-benzothiadiazepine, Mw. 696.89.

This compound is prepared as described in Example 2 of WO3022286.

Example 2

1,1-Dioxo-3,3-dibutyl-5-phenyl-7-methylthio-8-(N—{(R)-α-[N'—((S)-1-carboxyethyl) carbamoyl]benzyl} carbamoylmethoxy)-2,3,4,5-tetrahydro-1,5-benzothiazepine, Mw. 709.92.

This compound is prepared as described in Example 2 of WO03106482.

Example 3

1,1-Dioxo-3,3-dibutyl-5-phenyl-7-methylthio-8-(N—{(R)-α-[N—((S)-1-carboxypropyl) carbamoyl]benzyl}carbamoylmethoxy)-2,3,4,5-tetrahydro-1,2,5-benzothiadiazepine, Mw. 724.94.

This compound is prepared as described in Example 6 of WO3022286.

Example 4

1,1-Dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine, Mw. 757.01.

This compound is prepared as described in Example 7 of WO3022286.

Example 5

1,1-Dioxo-3,3-dibutyl-5-phenyl-7-methylthio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine, Mw. 740.94.

This compound is prepared as described in Example 29 of WO3022286.

Example 6

1,1-Dioxo-3,3-dibutyl-5-phenyl-7-methylthio-8-(N—{(R)-α-[N—((R)-1-carboxy-2-methylthioethyl)carbamoyl]-4-hydroxybenzyl}carbamoylmethoxy)-2,3,4,5-tetrahydro-1,2,5-benzothiadiazepine, Mw. 773.00.

This compound is prepared as described in Example 30 of WO3022286.

Example 7

1,1-Dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine, Mw. 738.97.

This compound is prepared as described in Example 15 of WO3022286.

Example 8

1,1-Dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine, Mw. 756.94.

This compound is prepared as described in Example 26 of WO3022286.

Example 9

1,1-Dioxo-3,3-dibutyl-5-phenyl-7-methylthio-8-(N—{(R)-α-[N—((S)-1-carboxybutyl) carbamoyl]-4-hydroxybenzyl}carbamoylmethoxy)-2,3,4,5-tetrahydro-1,2,5-benzothiadiazepine, Mw. 754.97.

This compound is prepared as described in Example 28 of WO3022286.

Example 10

1,1-Dioxo-3,3-dibutyl-5-phenyl-7-methylthio-8-(N—{(R)-α-[N—((S)-1-carboxyethyl) carbamoyl]benzyl}carbamoylmethoxy)-2,3,4,5-tetrahydro-1,2,5-benzothiadiazepine, Mw. 710.91.

This compound is prepared as described in Example 5 of WO3022286.

Example 11

1,1-Dioxo-3,3-dibutyl-5-phenyl-7-methylthio-8-(N—{(R)-α-[N'—((S)-1-carboxypropyl) carbamoyl]-4-hydroxybenzyl} carbamoylmethoxy)-2,3,4,5-tetrahydro-1,5-benzothiazepine, Mw. 739.95.

This compound is prepared as described in Example 1 of WO3022286.

Example 12

1,1-Dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine, Mw. 726.91.

This compound is prepared as described in Example 11 of WO3022286.

Example 13

1,1-Dioxo-3,3-dibutyl-5-phenyl-7-methylthio-8-(N—{(R)-α-[N—((S)-1-carboxy-2-methylpropyl)carbamoyl]-4- hydroxybenzyl}carbamoylmethoxy)-2,3,4,5-tetrahydro-1,2,5-benzothiadiazepine, Mw. 754.97.

This compound is prepared as described in Example 27 of WO3022286.

Example 14

1,1-Dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine, Mw. 695.90.

This compound is prepared as described in Example 43 of WO0250051.

Example 15

Pharmaceutical Effect Mean Inhibitory Effect (%)

ISBT Hu HEK Uptake SPA 13203 IBAT HUM Ileal Bile Acid Transporter Human HEK Glycocholic acid Uptake Radiometric—SPA Inhibitor IC50 Mean IC50 (nM) was determined for the compounds of examples 1-14

Test System

Animals

Species Mouse; Strain ApoE knock out; Sub strain C57BL/6; Sex Female; Total No. of animals 70; Body weight range 20 g to 22 g; Supplier Möllegaard's Breeding (Skensved, Denmark); Identification method ID cards (bar code).

Acclimatisation At least one week at the Section of Laboratory; Animal Resource at AstraZeneca; Housing conditions Kept five by five in cages (Makrolon III, 7 dm2) in a room with regulated temperature (22° C.), relative humidity (40% to 60%) and a 12/12 hours light/dark cycle. Diet Free access to R3 pellets (Lactamin, Vadstena, Sweden) during the housing and experimental period. Water, free access to tap water during the housing and experimental period.

Bedding Sprinkle bedding of aspen wood (Tapvei, Finland).

Experimental Procedures

The animals were orally administered vehicle (n=3) or the compound of Example 14 (0.156 (n=3), 0.625 (n=3) or 2.5 µmol/kg (n=3)) at 13:00 o'clock on the experimental day. Thirty minutes later, a trace amount of $^{75}$SeHCAT ($^{75}$Se-homo-tauro-cholic acid) (0.1 mCi per 0.1 mL per mouse) was orally given to each mouse. Twenty-four hours after $^{75}$SeHCAT administration, the animals were killed by CO2 inhalation. At sacrifice, the gall bladder and the whole intestine were removed, and the faeces during the 24-hour period after $^{75}$SeHCAT administration was collected for each mouse. The gamma radioactivities of $^{75}$SeHCAT in the faeces and in the gall bladder-intestine were separately counted by 1282 CompuGamma CS Gamma counter (Wallac oy, Turku, Finland). The stability as well as the quantity of the $^{75}$SeHCAT administered to each mouse, were controlled with an additional $^{75}$SeHCAT aliquot following the same experimental process as other tested samples in the study.

Data Analysis

The sum of the gamma counts from both the faeces and the gall bladder-intestine was considered as the total recovered $^{75}$SeHCAT, which was averaged around 85% of the total $^{75}$SeHCAT administered to each mouse. Of the recovered radioactivity of $^{75}$SeHCAT, the percentage of the $^{75}$SeHCAT detected in the faeces was considered as the faecal excretion while that in the gall bladder-intestine as body retention. Inhibitory effect of the compound of Example 14 on $^{75}$SeHCAT intestinal absorption was calculated following the $^{75}$SeHCAT body retention and the faecal excretion, and the ED50 of the compound was estimated following the dose-effect curve.

Results

The mean IBAT inhibitory effect (%) at a dose (µmol/kg): 0.156 was determined for the compounds of examples 1-14 and is reported in Table 1.

TABLE 1

| Example | Structure | % inhibition 0.156 µmol/kg | Mean IC50 nM |
|---|---|---|---|
| 1. | 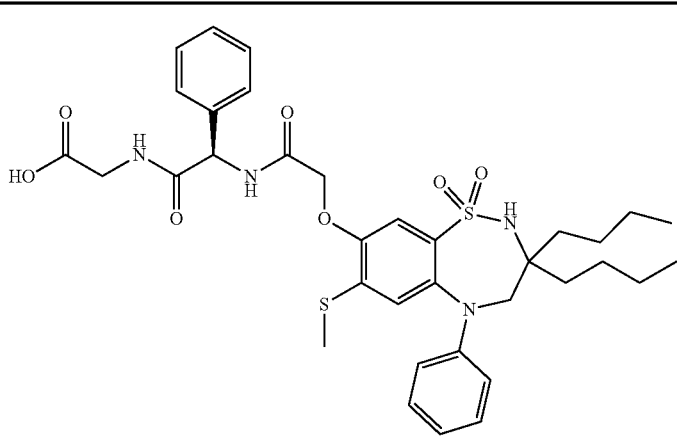 | 43 | 0.45 |

TABLE 1-continued
| Example | Structure | % inhibition 0.156 μmol/kg | Mean IC50 nM |
|---|---|---|---|
| 2. | 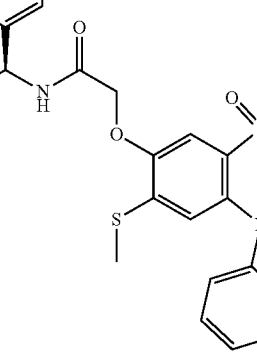 | 55 | 0.39 |
| 3. | 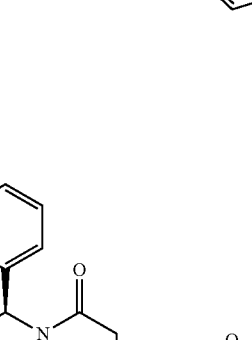 | 63 | 0.18 |
| 4. | 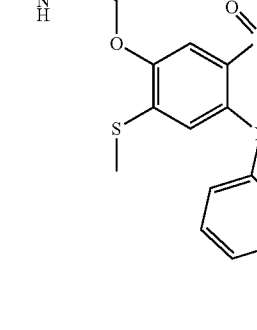 | 63 | 0.35 |

TABLE 1-continued

| Example | Structure | % inhibition 0.156 μmol/kg | Mean IC50 nM |
|---|---|---|---|
| 5. | 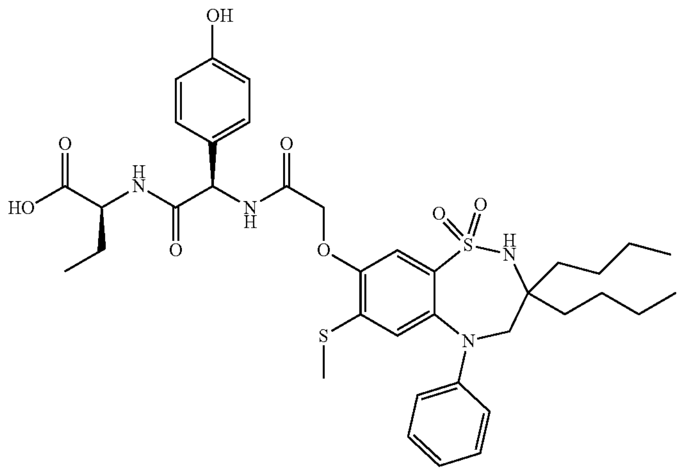 [SMILES: CCCCC1(CCCC)CN(c2ccccc2)c2cc(SC)c(OCC(=O)N[C@@H](C(=O)N[C@@H](CC)C(=O)O)c3ccc(O)cc3)cc2S(=O)(=O)N1] | 74 | 0.16 |
| 6. | 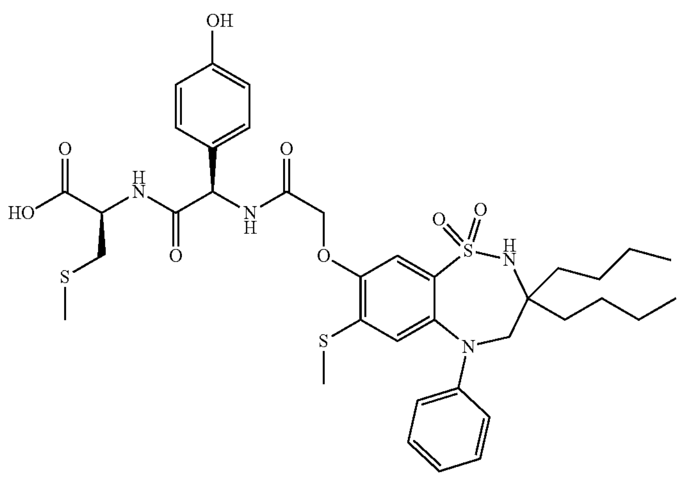 [SMILES: CCCCC1(CCCC)CN(c2ccccc2)c2cc(SC)c(OCC(=O)N[C@@H](C(=O)N[C@@H](CSC)C(=O)O)c3ccc(O)cc3)cc2S(=O)(=O)N1] | 59 | — |
| 7. | 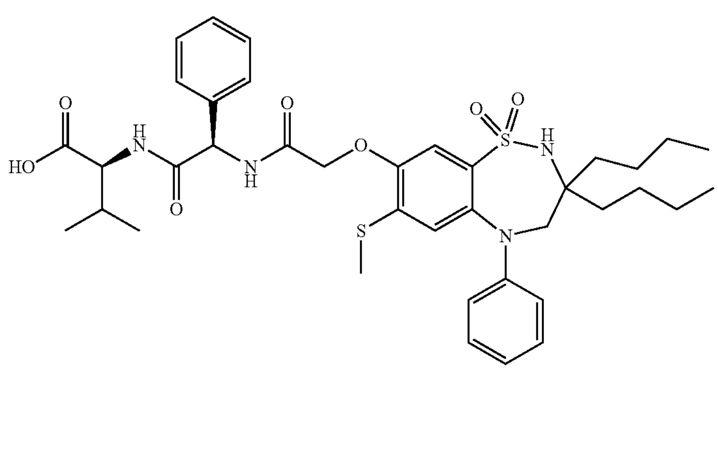 [SMILES: CCCCC1(CCCC)CN(c2ccccc2)c2cc(SC)c(OCC(=O)N[C@@H](C(=O)N[C@H](C(=O)O)C(C)C)c3ccccc3)cc2S(=O)(=O)N1] | 66 | 0.36 |

TABLE 1-continued

| Example | Structure | % inhibition 0.156 μmol/kg | Mean IC50 nM |
|---|---|---|---|
| 8. | 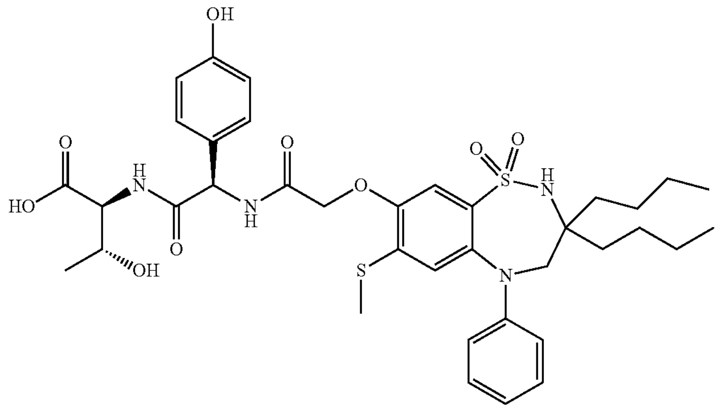 [SMILES: CCCCC1(CCCC)CN(c2ccccc2)c2cc(SC)c(OCC(=O)N[C@@H](C(=O)N[C@H](C(=O)O)[C@@H](C)O)c3ccc(O)cc3)cc2S(=O)(=O)N1] | 46 | 0.11 |
| 9. | 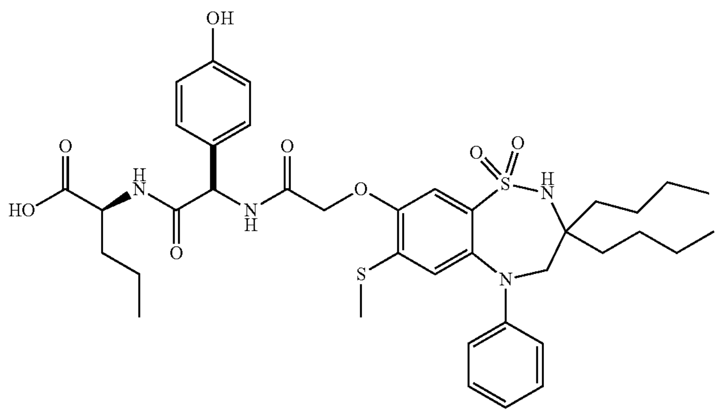 [SMILES: CCCCC1(CCCC)CN(c2ccccc2)c2cc(SC)c(OCC(=O)N[C@@H](C(=O)N[C@@H](CCC)C(=O)O)c3ccc(O)cc3)cc2S(=O)(=O)N1] | 67 | — |
| 10. | 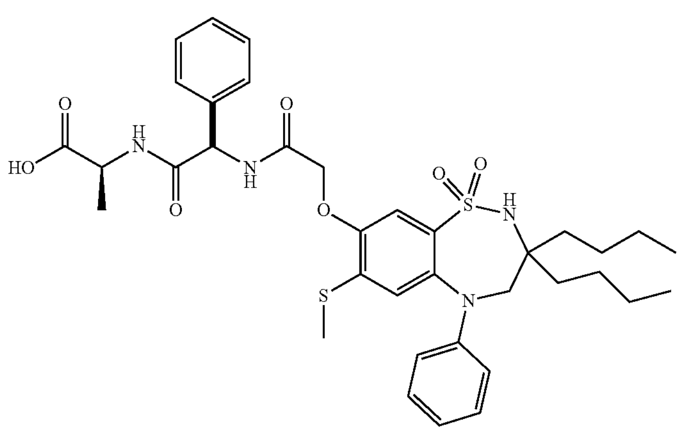 [SMILES: CCCCC1(CCCC)CN(c2ccccc2)c2cc(SC)c(OCC(=O)N[C@@H](C(=O)N[C@@H](C)C(=O)O)c3ccccc3)cc2S(=O)(=O)N1] | 68 | 0.2 |

TABLE 1-continued

| Example | Structure | % inhibition 0.156 μmol/kg | Mean IC50 nM |
|---|---|---|---|
| 11. | 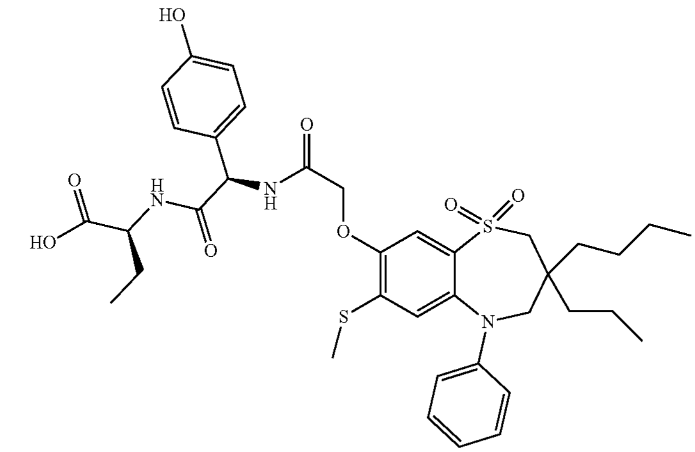 [SMILES: CCCCC1(CCC)CN(c2ccccc2)c2cc(SC)c(OCC(=O)N[C@@H](C(=O)N[C@@H](CC)C(=O)O)c3ccc(O)cc3)cc2S(=O)(=O)C1] | 63 | 0.15 |
| 12. | 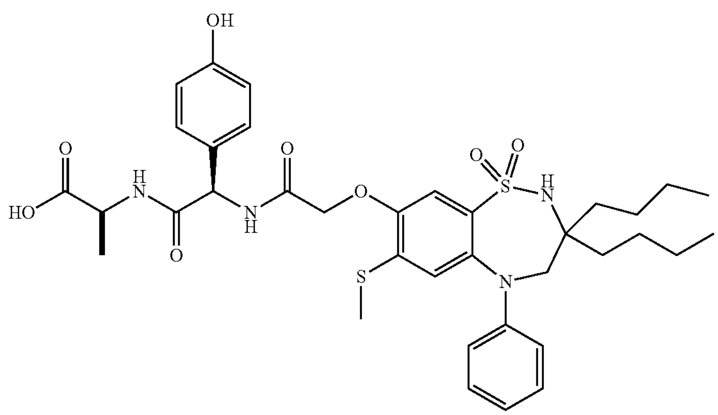 [SMILES: CCCCC1(CCCC)CN(c2ccccc2)c2cc(SC)c(OCC(=O)N[C@@H](C(=O)N[C@@H](C)C(=O)O)c3ccc(O)cc3)cc2S(=O)(=O)N1] | 63 | 0.3 |
| 13. | 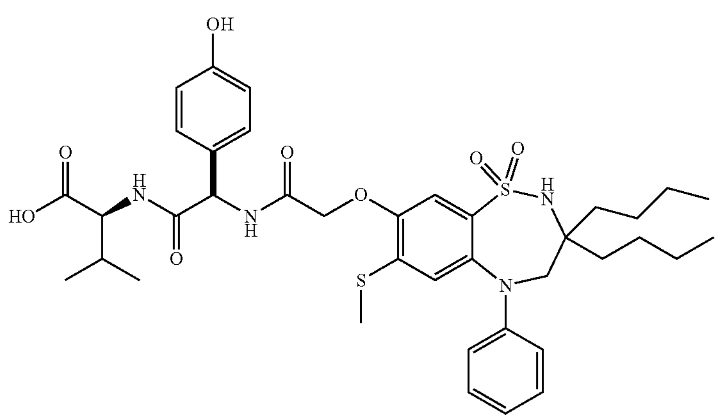 [SMILES: CCCCC1(CCCC)CN(c2ccccc2)c2cc(SC)c(OCC(=O)N[C@@H](C(=O)N[C@H](C(=O)O)C(C)C)c3ccc(O)cc3)cc2S(=O)(=O)N1] | 68 | 0.13 |

TABLE 1-continued

| Example | Structure | % inhibition 0.156 μmol/kg | Mean IC50 nM |
|---|---|---|---|
| 14. | 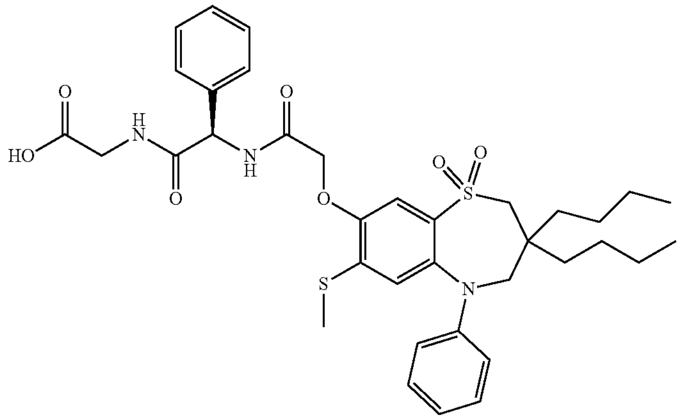 [SMILES: CCCCC1(CCCC)CN(c2ccccc2)c2cc(SC)c(OCC(=O)N[C@@H](C(=O)NCC(=O)O)c3ccccc3)cc2S(=O)(=O)C1] | 28 | 1.2 |

Example 16

In Vivo Animal Model of Primary Sclerosing Cholangitis (PSC)

A genetic mice with targeted disruption of the Multidrug resistant Mdr2 (Abcb4) gene encoding a canalicular phospholipid flippase (Mdr2−/− mice) spontaneously develop sclerosing cholangitis with macroscopic and microscopic features of human Primary sclerosing cholangitis. Bile duct injury in these mice is linked to defective biliary phospholipid secretion resulting in an increased concentration of free non-micellar bile acids which subsequently cause bile duct epithelial cell (cholangiocyte) injury, pericholangitis, periductal fibrosis with ductular proliferation and finally sclerosing cholangitis. Gene expression profiling has revealed remarkable similarities between Mdr2−/− and human PSC. In analogy to the Mdr2−/− mouse model of sclerosing cholangitis, Multidrug resistant protein MDR3/ABCB4 (the human orthologue of rodent Mdr2/Abcb4) defects play a role in the pathogenesis of various cholangiopathies in humans. MDR3 variants play a role as a modifier gene in the pathogenesis of various cholangiopathies such as PSC, Primary Biliary cirrhosis (PBC) and adulthood idiopathic ductopenia/biliary fibrosis.

Mdr2−/− mice were given daily oral doses of the compound of Example 14 by gavage for 2-4 weeks and controls were dosed the vehicle in the same way. Serum liver tests, liver histology and fibrosis were investigated. The compound of Example 14 improves liver tests, liver histology and fibrosis.

Example 17

A formulation for delayed release of the IBAT inhibitor having the following composition is be prepared:

| Substance | amount/capsule (mg) |
|---|---|
| IBAT inhibitor compound Example 14 | 10 |
| Non pareil spheres | 500 |
| Ethyl cellulose | 2 |

-continued

| Substance | amount/capsule (mg) |
|---|---|
| Hydroxypropylmethyl cellulose | 10 |
| Eudragit L100-55, CAS No: 25212 - 88 - 8 | 25 |
| Triethylcitrate | 2.4 |

The IBAT inhibitor compound of Example 14 is dissolved together with ethyl cellulose and hydroxypropyl cellulose in ethanol 99%. The mixture is then sprayed onto the nonpareil spheres in a fluidized bed apparatus. Thereafter, the pellets are dried and aerated to remove residual ethanol. The Eudragit L100-55 dispersion with addition of triethyl citrate is then sprayed onto the drug beads in a fluidized bed apparatus. Subsequently, the coated beads are filled in hard gelatine capsules after drying and sieving.

Example 18

A formulation for delayed release of the IBAT inhibitor having the following composition is prepared:

| Ingredient | amount/tablet (mg) |
|---|---|
| IBAT inhibitor compound Example 14 | 10 |
| Silicon dioxide | 200 |
| Povidone K-25 | 20 |
| Eudragit FS30D, CAS no: 26936 - 24 - 3 | 30 |
| Microcrystalline cellulose | 250 |
| Sodium stearyl fumarate | 5 |

The IBAT inhibitor compound of Example 14 is suspended in water and sprayed onto silicon dioxide cores of a predefined size in a fluidized bed apparatus. The drug pellets are dried in an oven at 40° C. for 24 h. Thereafter, a layer of Povidone K-25 is applied on the beads from an ethanolic solution in a fluidized bed apparatus. A final coat of Eudragit FS30D dispersion is applied thereafter in a fluidized bed. The coated beads are mixed with microcrystalline cellulose and sodium stearyl fumarate in a mixer and subsequently compressed to tablets.

Example 19

An IBAT inhibitor—colesevelam combination tablet with immediate release of the IBAT inhibitor and colon release of the bile acid binder having the following composition is prepared:

| Ingredient | amount/tablet (mg) |
|---|---|
| Core | |
| Colesevelam hydrochloride | 400 |
| Microcrystalline cellulose | 150 |
| Hydroxypropyl methyl cellulose | 50 |
| Colloidal silicon dioxide | 10 |
| Magnesium stearate | 5 |
| Colon release layer | |
| Eudragit FS30D | 60 |
| PlasACRYL T20, CAS no 123-94-4 | 6 |
| IBAT inhibitor layer | |
| IBAT inhibitor Example 14 | 7 |
| Hydroxypropylmethyl cellulose | 12 |
| Croscarmellose sodium | 6 |
| Protective coating | |
| Hydroxypropylmethyl cellulose | 12 |
| Polyethylene glycol | 2 |

Colesevelam hydrochloride, microcrystalline cellulose and colloidal silicon dioxide are mixed and granulated with hydroxypropyl methyl cellulose dissolved in water. The granules are dried and mixed with magnesium stearate and compressed to tablets. The EUDRAGIT FS30D dispersion and water are stirred into the PlasACRYL T20 and sprayed onto the core tablets using a suitable coating machine. The IBAT inhibitor coating suspension is prepared by mixing the IBAT inhibitor, hydroxypropyl methyl cellulose and croscarmellose sodium in water and sprayed onto the tablet cores with the colon release layer using a suitable coating machine. Finally the protective coating solution of hydroxypropylmethyl cellulose and polyethylene glycol are sprayed onto the tablets using a suitable coating machine.

Example 20

A Colesevelam colon release tablet having the following composition is prepared:

| Ingredient | amount/tablet (mg) |
|---|---|
| Core | |
| Colesevelam hydrochloride | 400 |
| Microcrystalline cellulose | 150 |
| Hydroxypropyl methyl cellulose | 50 |
| Colloidal silicon dioxide | 10 |
| Magnesium stearate | 5 |
| Colon release layer | |
| Amylose | 30 |
| Eudragit S100 | 60 |
| Triethylcitrate | 6 |
| Glycerolmonostearate | 3 |

Colesevelam hydrochloride, microcrystalline cellulose and colloidal silicon dioxide are mixed and granulated with hydroxypropyl methyl cellulose dissolved in water. The granules are dried and mixed with magnesium stearate and compressed to tablets. Amylose, Eudragit 100, triethylcitrate and glycerolmonosterate are dissolved in suitable solvents and sprayed onto the tablet cores using a suitable coating machine.

The invention claimed is:

1. A method for treating a bile acid dependent disease in a subject, the method comprising orally administering to a subject in need of such treatment a therapeutically effective amount of an IBAT inhibitor, wherein the IBAT inhibitor is 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine, or a pharmaceutically acceptable salt thereof, wherein the bile acid dependent disease is selected from the group consisting of Alagille syndrome (ALGS), progressive familial intrahepatic cholestasis (PFIC), primary biliary cirrhosis (PBC), liver fibrosis, nonalcoholic fatty liver disease, non alcoholic steatohepatitis (NASH), primary sclerosing cholangitis (PSC), intrahepatic cholestasis, extrahepatic cholestasis, a malignancy causing obstruction of the biliary tree, drug-induced cholestasis, cholestasis of pregnancy, and combinations thereof.

2. The method of claim 1, wherein the IBAT inhibitor is administered in combination with ursodeoxycholic acid or nor-ursodeoxycholic acid.

3. The method of claim 1, wherein the subject has pruritus as a symptom of the bile acid dependent disease.

4. The method of claim 1, wherein the subject has pruritus as a comorbidity.

5. The method of claim 1, wherein the bile acid dependent disease is selected from the group consisting of: Alagille syndrome (ALGS), progressive familial intrahepatic cholestasis (PFIC), intrahepatic cholestasis, extrahepatic cholestasis, and combinations thereof.

6. The method of claim 1, wherein the bile acid dependent disease is a malignancy causing obstruction of the biliary tree.

7. The method of claim 1, wherein the bile acid dependent disease is intrahepatic cholestasis, extrahepatic cholestasis, or a combination thereof.

8. The method of claim 1, wherein the concentration of serum bile acids in the subject is decreased following administration of the IBAT inhibitor.

9. The method of claim 1, wherein the concentration of liver bile acids in the subject is decreased following administration of the IBAT inhibitor.

10. The method of claim 1, wherein the subject is a pediatric subject.

* * * * *